US007011033B2

(12) United States Patent
Sargent, Jr. et al.

(10) Patent No.: US 7,011,033 B2
(45) Date of Patent: Mar. 14, 2006

(54) METHOD AND APPARATUS FOR CORD ATTACHMENT

(75) Inventors: Raymond Albert Sargent, Jr., Mason, OH (US); Robert Paul Cassoni, Washington Township, OH (US); David Stuart Howell, II, Washington Township, OH (US); Lucy Margaret Davey, Ringwood (GB)

(73) Assignee: The Procter & Gamble Company, Cincinnati, OH (US)

( * ) Notice: Subject to any disclaimer, the term of this patent is extended or adjusted under 35 U.S.C. 154(b) by 295 days.

(21) Appl. No.: 10/610,075

(22) Filed: Jun. 30, 2003

(65) Prior Publication Data

US 2004/0261237 A1 Dec. 30, 2004

(51) Int. Cl.
*D05B 23/00* (2006.01)
(52) U.S. Cl. ................................. 112/475.17
(58) Field of Classification Search ........... 112/475.17, 112/265, 104, 475.08, 156, 429; 28/120; 289/1.5, 1.2; 128/112.1; 604/13, 15, 18; 426/77, 82, 83; 53/134.2
See application file for complete search history.

(56) References Cited

U.S. PATENT DOCUMENTS

| 237,966 | A | * | 2/1881 | Elliott | 112/475.17 |
|---|---|---|---|---|---|
| 461,793 | A | * | 10/1891 | Briggs | 112/475.17 |
| 2,462,178 | A | | 2/1949 | Ganz | |
| 3,677,034 | A | | 7/1972 | Simpson | |
| 3,749,094 | A | | 7/1973 | Duncan | |
| 3,766,921 | A | | 10/1973 | Dulle | |
| 3,794,029 | A | | 2/1974 | Dulle | |
| 3,811,445 | A | | 5/1974 | Dostal | |
| 3,812,856 | A | | 5/1974 | Duncan | |
| 3,814,469 | A | | 6/1974 | Simon | |
| 3,815,601 | A | | 6/1974 | Schaefer | |
| 3,834,389 | A | | 9/1974 | Dulle | |
| 3,852,847 | A | | 12/1974 | Etz | |
| 3,856,013 | A | | 12/1974 | Dulle | |
| 3,863,636 | A | | 2/1975 | Johnson | |
| 3,940,169 | A | | 2/1976 | Kock | |
| 3,948,257 | A | | 4/1976 | Bossak | |
| 3,957,004 | A | | 5/1976 | Ketterer | |
| 3,965,905 | A | | 6/1976 | Schoenholz | |
| 3,970,022 | A | | 7/1976 | Kopatz et al. | |
| 3,976,075 | A | | 8/1976 | Chinai | |
| 4,169,004 | A | | 9/1979 | Kock | |
| 4,332,251 | A | | 6/1982 | Thompson | |
| 4,366,765 | A | * | 1/1983 | Hoekstra | 112/429 |
| 4,475,911 | A | | 10/1984 | Gellert | |
| 4,699,618 | A | | 10/1987 | Sustmann | |
| 4,923,440 | A | | 5/1990 | Genaro | |

(Continued)

*Primary Examiner*—Ismael Izaguirre
(74) *Attorney, Agent, or Firm*—Ingrid N. Hickman; Kevin C. Johnson; Steven W. Miller

(57) ABSTRACT

An apparatus and method for attaching a cord to a piece of material. The material has a first side and a second side. The apparatus has a frame, a punch pin, a spear, and a comber. The comber is movably mounted to the frame. The comber is adapted to create slack in the cord. The punch pin is movably mounted to the frame. The punch pin is adapted to receive the cord and penetrate the material. The punch pin pulls the cord from the first side of the material through to the second side of the material. The punch pin is adapted to form an open loop on the second side of the material and the spear draws the cord through the open loop.

2 Claims, 24 Drawing Sheets

U.S. PATENT DOCUMENTS

| | | |
|---|---|---|
| 5,084,038 A | 1/1992 | Sheldon |
| 5,370,633 A | 12/1994 | Villalta |
| 5,383,891 A | 1/1995 | Walker |
| 5,395,308 A | 3/1995 | Fox |
| 5,458,589 A | 10/1995 | Comin-DuMong |
| 5,533,990 A | 7/1996 | Yeo |
| 5,542,914 A | 8/1996 | Van Iten |
| 5,566,435 A | 10/1996 | Brown, Jr. |
| 5,657,712 A | 8/1997 | Romagnoli |
| 5,659,934 A | 8/1997 | Jessup |
| 5,674,239 A | 10/1997 | Zadini |
| 5,738,646 A | 4/1998 | Fox |
| 5,797,243 A | 8/1998 | Tagliaferri |
| 5,827,256 A | 10/1998 | Balzar |
| 5,873,971 A | 2/1999 | Balzar |
| 5,891,123 A | 4/1999 | Balzar |
| 6,142,984 A | 11/2000 | Brown |
| 6,213,040 B1 | 4/2001 | Shepard |
| 6,216,620 B1 | 4/2001 | Shepard |
| 6,312,419 B1 | 11/2001 | Durel-Crain |
| 6,343,558 B1 | 2/2002 | Shepard |
| 6,654,992 B1 * | 12/2003 | Rajala et al. .................. 28/120 |
| 6,746,699 B1 * | 6/2004 | Lohrey et al. ................ 426/83 |

* cited by examiner

METHOD AND APPARATUS FOR CORD ATTACHMENT

FIELD OF INVENTION

The present invention relates to the fields of attaching a strand of material, cord, or wire to one or more pieces of material.

BACKGROUND OF THE INVENTION

The attachment of a strand of material, cord, or wire to one or more pieces of material presents challenges to today's high speed manufacturing processes. The tampon industry is an example. In the tampon industry, the rate at which the products are produced require that a high speed manufacturing process be employed.

Current tampon designs employ a withdrawal string, usually a cotton cord, to allow the user to remove the product after use. The cord must be firmly attached to the tampon pad, and must not shear the product or leave material behind upon withdrawal. Secure attachment or engagement of the withdrawal string to or around the tampon is of high importance so that there is no inadvertent detachment of the withdrawal string from the tampon while attempting to remove the tampon from the body—which would leave no easy means for removing the tampon from the body and may require the assistance of medical personnel.

The intent of a withdrawal string is that a portion or end of the withdrawal string remain outside the body for easy grasping while another end of the withdrawal string is secured to the tampon. For digital tampons and tampons used in tampon applicators, a looped withdrawal cord may be used. The withdrawal cord is looped around the tampon pledget and a portion of the loop remains outside the body. This means that instead of one, there are often two cord segments outside the body which then pass by the labia, through the introitus and into the vaginal cavity where they are engaged with the tampon.

One current method for attaching a cord to a pad involves sewing the cord to the pad, although this technique has a variety of disadvantages. The piercing of a cord by the thread actually weakens the cord, thereby requiring a thicker cord to meet any strength specifications. The use of thread to attach a cord to a pad introduces the possibility of thread breakage or jamming of the sewing apparatus. Current high speed industrial sewing machines operate at rates that are typically insufficient to feed a high speed production line. As a result, multiple sewing stations are required and their respective outputs must be merged to feed a single production line. Such multiple stations operating near their maximum rated speed, as well as the merging mechanism, increase the possibility and frequency of mechanical failures, jams, etc. Further, the reciprocating motion of traditional sewing machine movement, combined with the very thin and flexible handling qualities of thread, further increase the likelihood of jams, or mechanical failure.

Another method of attaching a cord to a pad involves punching of a cord once through the pad, and entanglement of the cord about the pad, i.e. with a knot or other restraining mechanism. Punching a cord once through a pad suffers from a lack of redundancy of attachment. Should the cord fail to puncture the pad, the needle fail to feed the cord properly, or the pad is misaligned, the cord will not be attached to the pad. Also, the force on the cord during the use of the product assembly is undesirably concentrated at the single point where the cord is attached to the pad. Cord entanglement does not offer the mechanical strength or integrity offered by a cord that is firmly attached to the pad since the cord can slip off. Simply tying a string to a pad in such a fashion creates a product which is prone to failure. Accordingly, a need exists for a cord attachment mechanism that is fast enough to support a subsequent high speed production line and which meets the reliability requirements of its users.

This application is directed to attaching a strand of material, cord or wire to one or more pieces of material and is particularly directed to an improved arrangement for the attachment of the string to the tampon pledget which provides easier facilitation of introducing the tampon into the body cavity and/or removal of the tampon from the body cavity.

SUMMARY OF THE INVENTION

The present invention relates to a method of attaching a cord to a piece of material. The inventive method is characterized by the steps of: providing a cord; providing a material having a first side and a second side; placing the second side of the material on top of the cord; engaging a portion of the cord; pushing the cord through the second side of the material to a first side of the material; creating a first open loop and a remaining loop on the first side of the material; and threading a first open loop through the remaining loop on the first side of the material.

The present invention relates to a method of attaching a cord to a piece of material. The inventive method is characterized by the steps of: providing a cord; providing a material having a first side and a second side; placing the second side of the material on top of the cord; engaging a portion of the cord; pushing the cord through the second side of the material to a first side of the material; creating a first open loop and a remaining open loop on the first side of the material; and threading a first open loop through the remaining open loop on the first side of the material.

The present invention relates to a method of attaching a cord to a piece of material. The inventive method is characterized by the steps of: providing a cord; providing a first material and a second material having a first side and a second side; pre-positioning the cord proximate a penetration point of the first material; contacting the penetration point with at least a portion of the punch pin; engaging the cord with the punch pin; penetrating the first material with the cord; and penetrating the second material with the cord.

The present invention relates to a method of attaching a cord to a piece of material. The inventive method is characterized by the steps of: providing a cord; providing a material having a first side and a second side; providing a comber; providing a punch pin with a first end and a second end; providing a spear; providing a cross pin; placing a cord on a surface: placing the second side of the material on top of the cord; moving the comber in a first direction which creates slack in the cord by engaging the cord with the comber; penetrating the material with a portion of the cord and the second end of the punch pin to form an open loop at the first side of the material with the punch pin; maintaining the open loop with the cross pin; and passing a portion of the cord through the open loop with the spear.

The present invention encompasses attaching a cord to a piece of material. The apparatus has a frame; a punch pin; a spear; and a comber. The comber is movably mounted to the frame. The comber is adapted to create slack in the cord. The punch pin is movably mounted to the frame. The punch pin is adapted to receive the cord and penetrate the material. The punch pin pulls the cord from the first side of the material through to the second side of the material. The punch pin is adapted to form an open loop on the second side of the material. The spear draws the cord through the open loop.

All documents cited are, in relevant part, incorporated herein by reference; the citation of any document is not to be construed as an admission that it is prior art with respect to the present invention.

DETAILED DESCRIPTION OF THE INVENTION

Figure 1A:
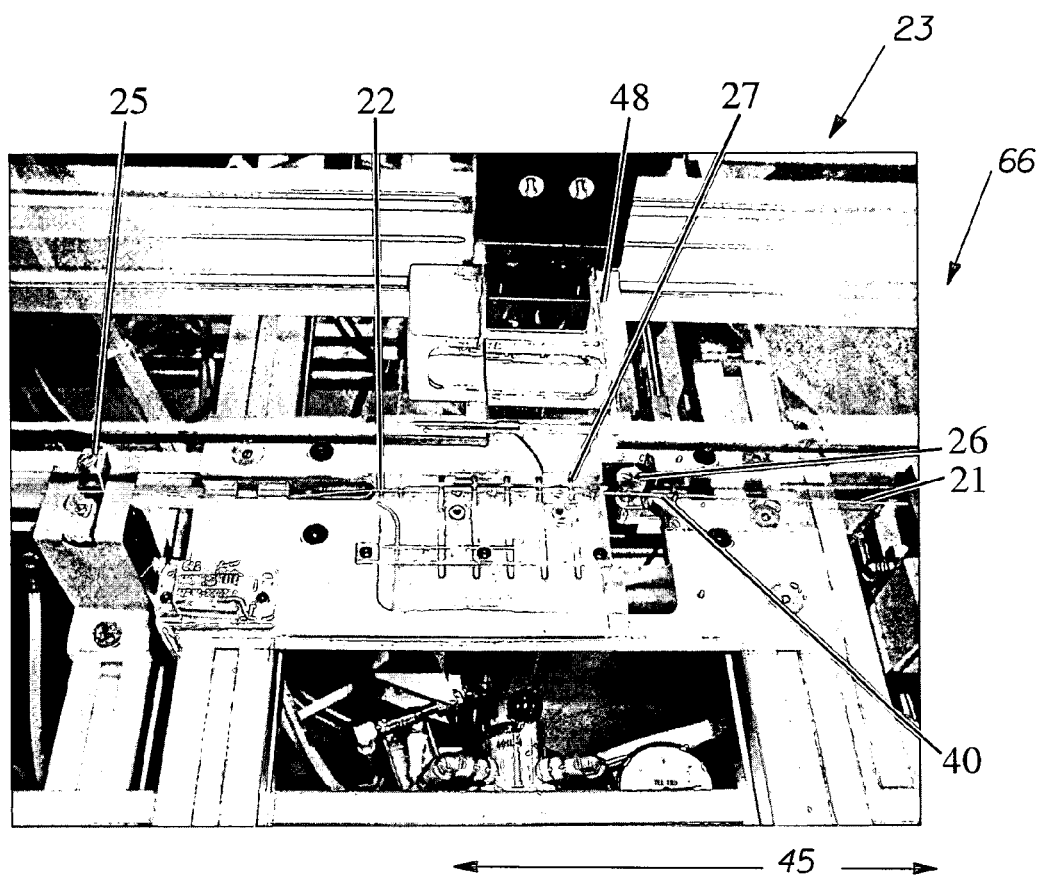
FIG. 1a is a perspective view of the lacing station.

The present invention provides a new and improved tampon article as well as a method of making a tampon with an attached cord, in particular tampons with more than one cord segment comprising a loop. Further, the method provides an improved process for attaching one or more cords or decorative cords not only to tampon pledgets, but also to fabrics and garments when producing decorative garments. There are several advantages to using the present method. First, conventional sewing techniques compromise string integrity by using the needle to penetrate the cord which is used to attach the pledget. Because the cord is not penetrated, the string-pad bond is stronger than current sewing attachment techniques. Second, the present invention eliminates the need of a needle to attach the cord to the pledget. The elimination of the needle eliminates the need to refurbish and replace needles. Third, the present method eliminates the use of extra thread to attach the cord to the pledget which results in decreased manufacturing cost.

Section A will provide terms which will assist the reader in best understanding the features of the invention, but not to introduce limitations in the terms inconsistent with the context in which they are used in this specification. These definitions are not intended to be limiting. Section B will discuss the different stages of the method of manufacturing a tampon. Section C will provide a description of a high speed manufacturing process.

A. Terms

The term "tampon" refers to any type of absorbent structure which is inserted into the vaginal canal or other body cavities for the absorption of fluid there from. Typically, tampons are constructed from a pledget of an absorbent material, which has been compressed and/or shaped in any or all of the width direction, the radial direction, and the axial direction, in order to provide a tampon which is of a size and stability to allow insertion within the vagina or other body cavity. A tampon has a "self-sustaining shape" when a tampon pledget has been compressed and/or shaped such that it assumes a general shape and size which is vaginally insertable absent external forces. It will be understood by one of skill in the art that this self-sustaining shape need not, and preferably does not, persist during actual use of the tampon. That is, once the tampon is inserted and begins to acquire fluid, the tampon may begin to expand and may lose its self-sustaining form.

As used herein, the terms "pledget" or "tampon pledget" are intended to be interchangeable and refer to a construction of absorbent material prior to the compression of such construction into a tampon as described above. Tampon pledgets are sometimes referred to as a tampon blank, or a softwind, or a pad, and the term "pledget" is intended to include such terms as well.

As used herein, the terms "vaginal cavity", "within the vagina", and "vaginal canal" are intended to be synonymous and refer to the internal genitalia of the human female in the prudendal region of the body. The term "vaginal canal" is intended to refer to the space located between the introitus of the vagina (sometimes referred to as the sphincter of the vagina) and the cervix and is not intended to include the interlabial space, including the floor of vestibule. The externally visible genitalia generally are not included within the term "vaginal canal" as used herein.

The term "digital tampon" refers to a tampon which is intended to be inserted into the vaginal canal with the user's finger and without the aid of an applicator. Thus, digital tampons are typically visible to the consumer prior to use rather than being housed in an applicator.

The term "cord" 21 refers to a long or slender flexible material often employed to transmit tensile forces, such as would be needed during typical tampon withdrawal from the body. The cord or cords 21 can be employed to attach two or more materials or used as decorative cording. The method can be used to attach or join two or more known materials of the same or different composition. For example, the materials to be attached or joined may be two absorbent materials to create personal hygiene products or two fabrics which may be used to create garments. Cord 21 cross-sections are often circular however they can take any shape depending on the form of the cord 21. Small width cords 21 are commonly referred to as strings while much larger width cords 21 can be referred to as ropes. A cord 21 can be comprised of single or usually multiple filaments or strands (such as of yarn or thread) woven or twisted or false-twisted together. Withdrawal cords useful in the present invention may be made of any suitable material known in the prior art and include cotton and rayon. For the purposes of this development, a cord 21 can also comprise a material from a strip of material resembling a tape, a ribbon, a soutache, a thread, a filament, or a braid, of which they can be made from nonwoven, woven, resin, extruded, solvent drawn, melt drawn, monofilamentous, or film-based components. In addition, the cord 21 can comprise a partial or fully integrated braided tail. Example material compositions include cotton, cellulose, rayon, polyolefins such as polyethylene or polypropylene, nylon, silk, Dacron (Registered), etc; though preferred compositions include cotton, rayon or polypropylene. Tampon cords 21 can range from 0.05 millimeters to 0.8 millimeters.

The term "withdrawal cord" or "withdrawal string" refers to one or more cords or cord segments attached to the tampon to permit ease for removing the tampon from the body.

B. Method

The method for attaching at least one cord 21 to a piece of material will now be explained with reference to FIGS. 1–12. The present method may use one cord 21, multiple cords 21, or multiple cord segments 21.

Figure 2A:
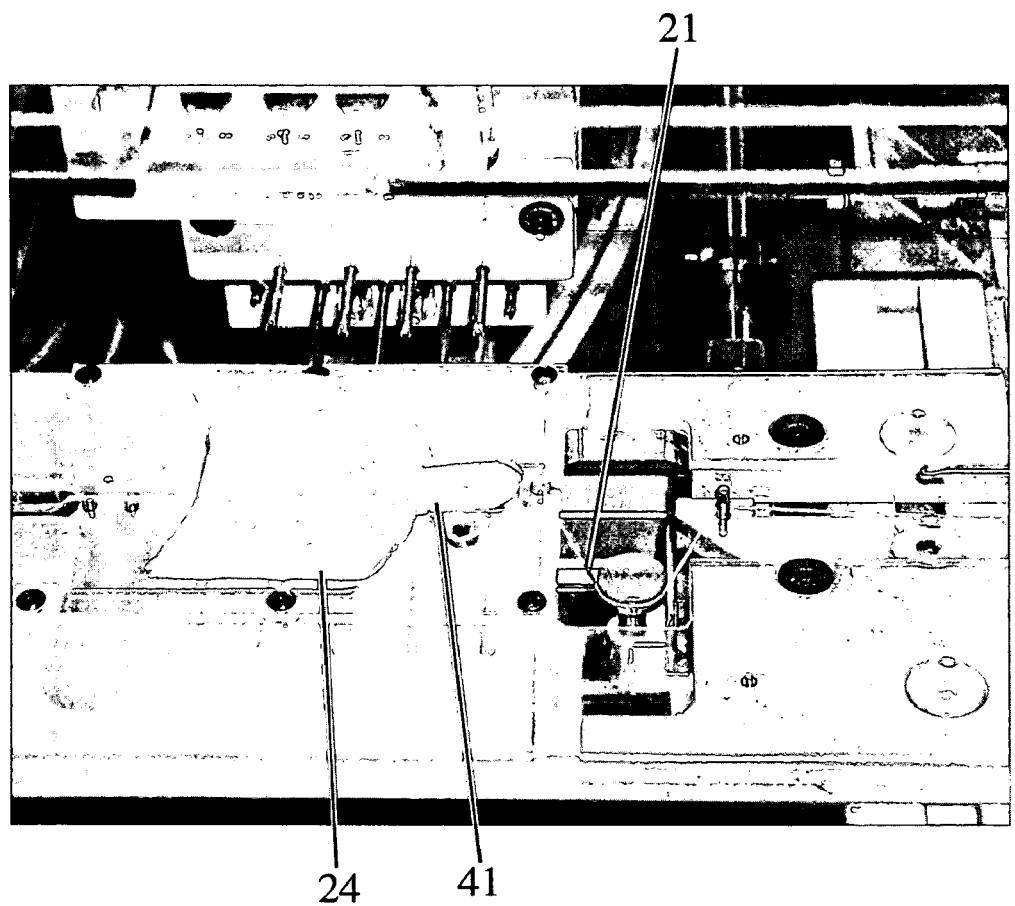
FIG. 2a is a perspective view of the lacing station.
Figure 3:
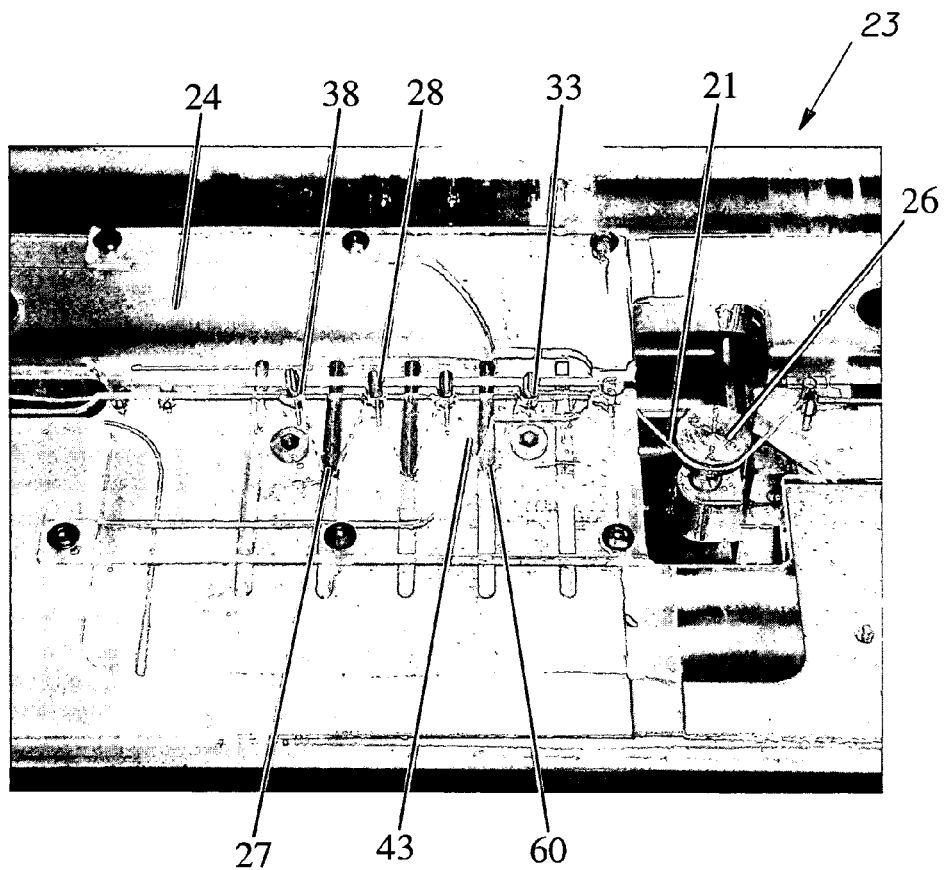
FIG. 3 is a perspective view of the lacing station.
Figure 4A:
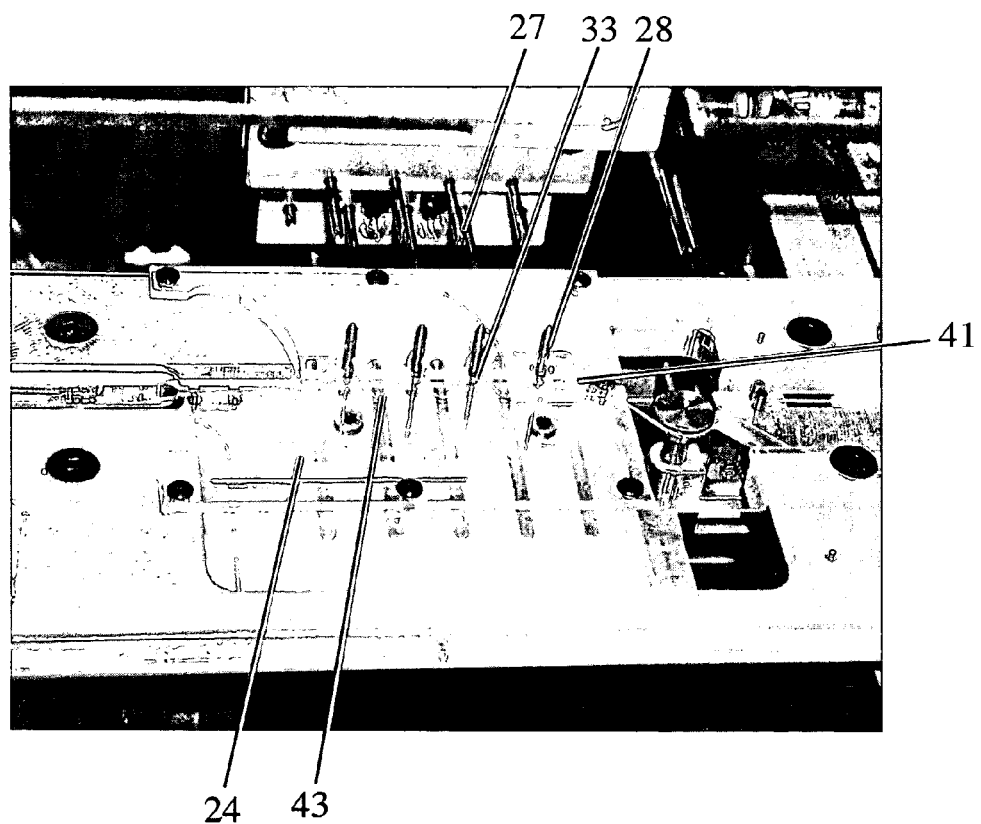
FIG. 4a is a perspective view of the lacing station.
Figure 5A:
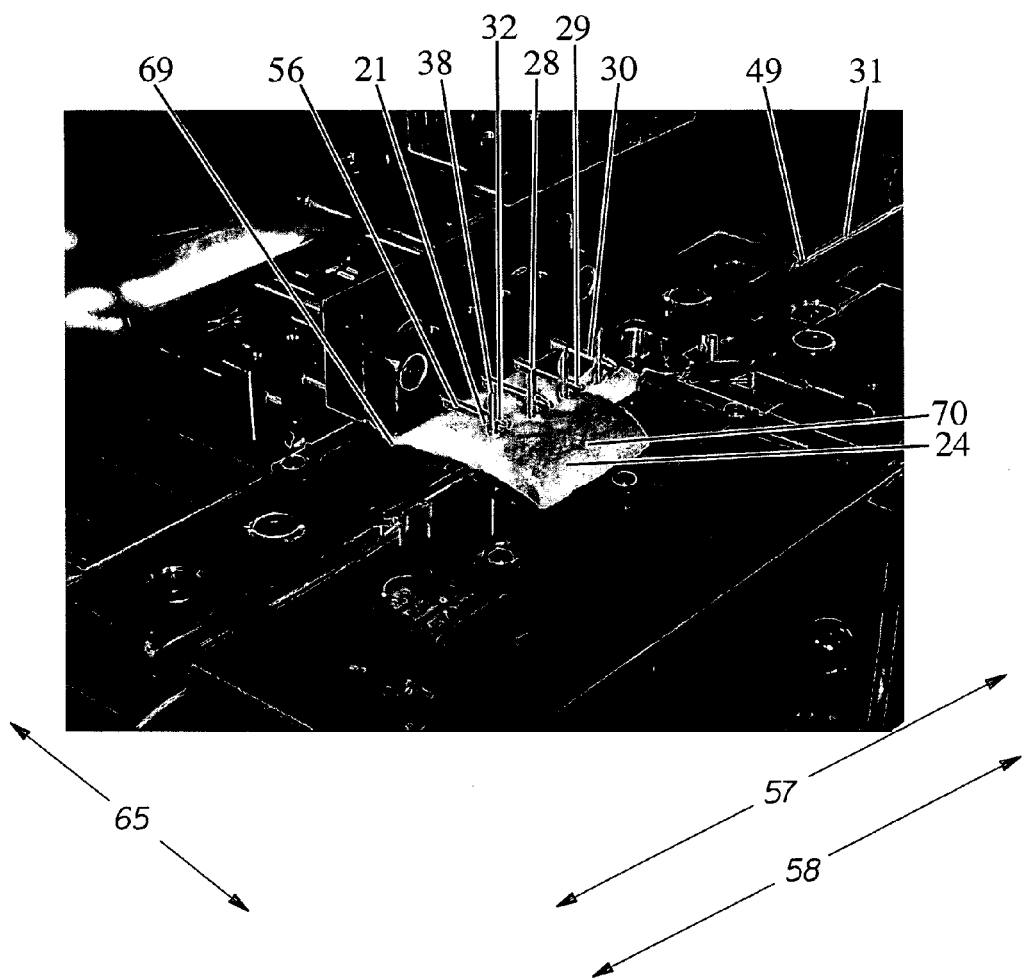
FIG. 5a is a perspective view of the lacing station.
Figure 6:
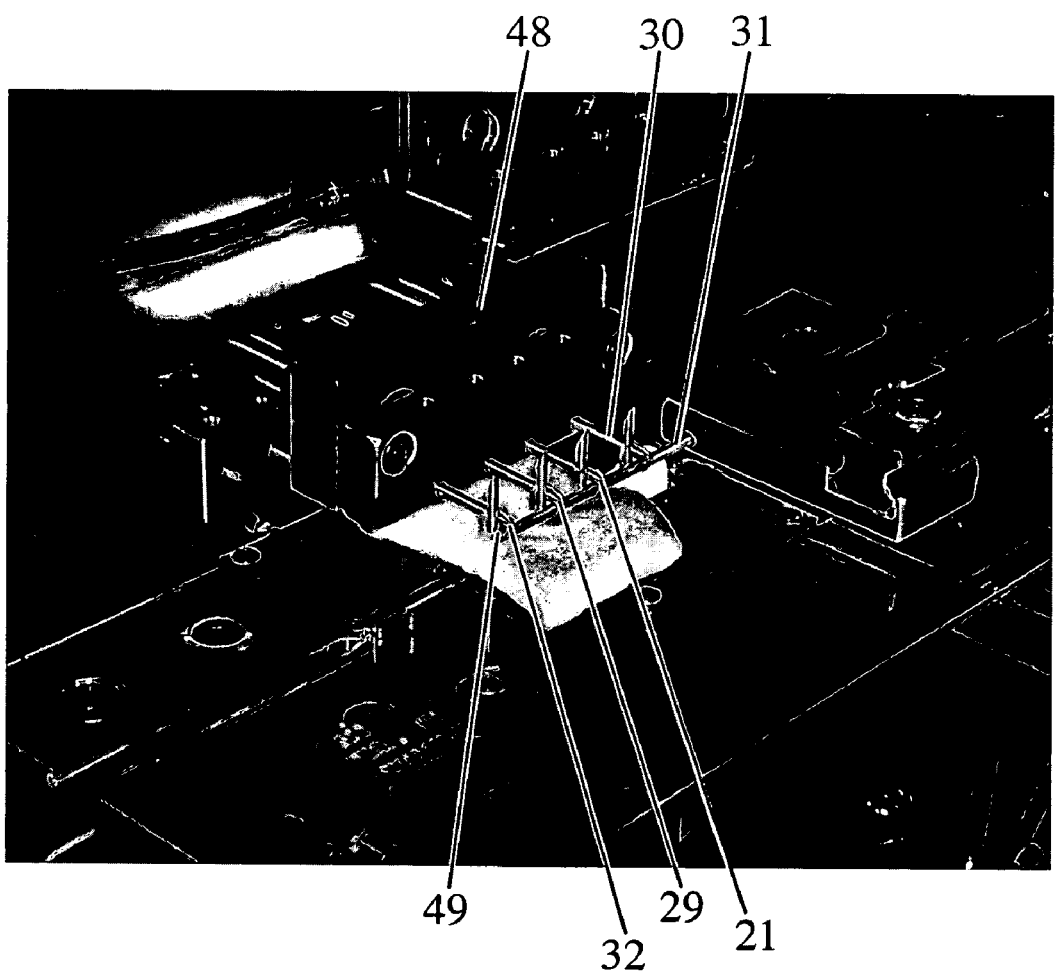
FIG. 6 is a perspective view of the lacing station.
Figure 7:
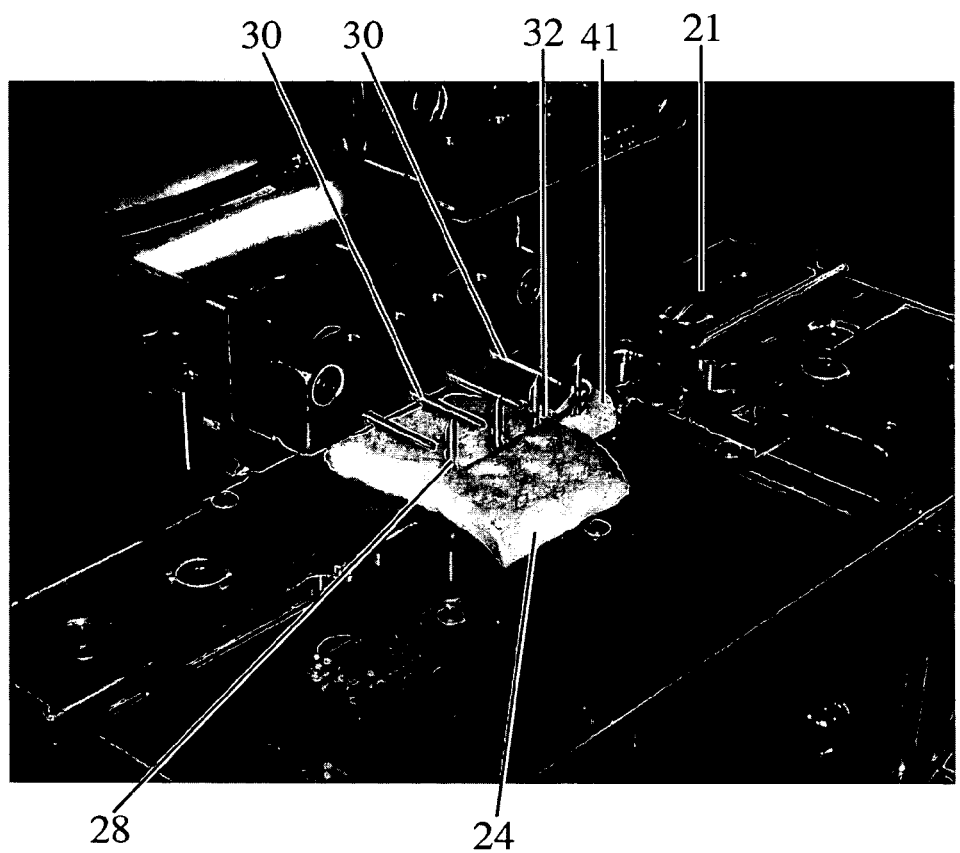
FIG. 7 is a perspective view of the lacing station.
Figure 8:
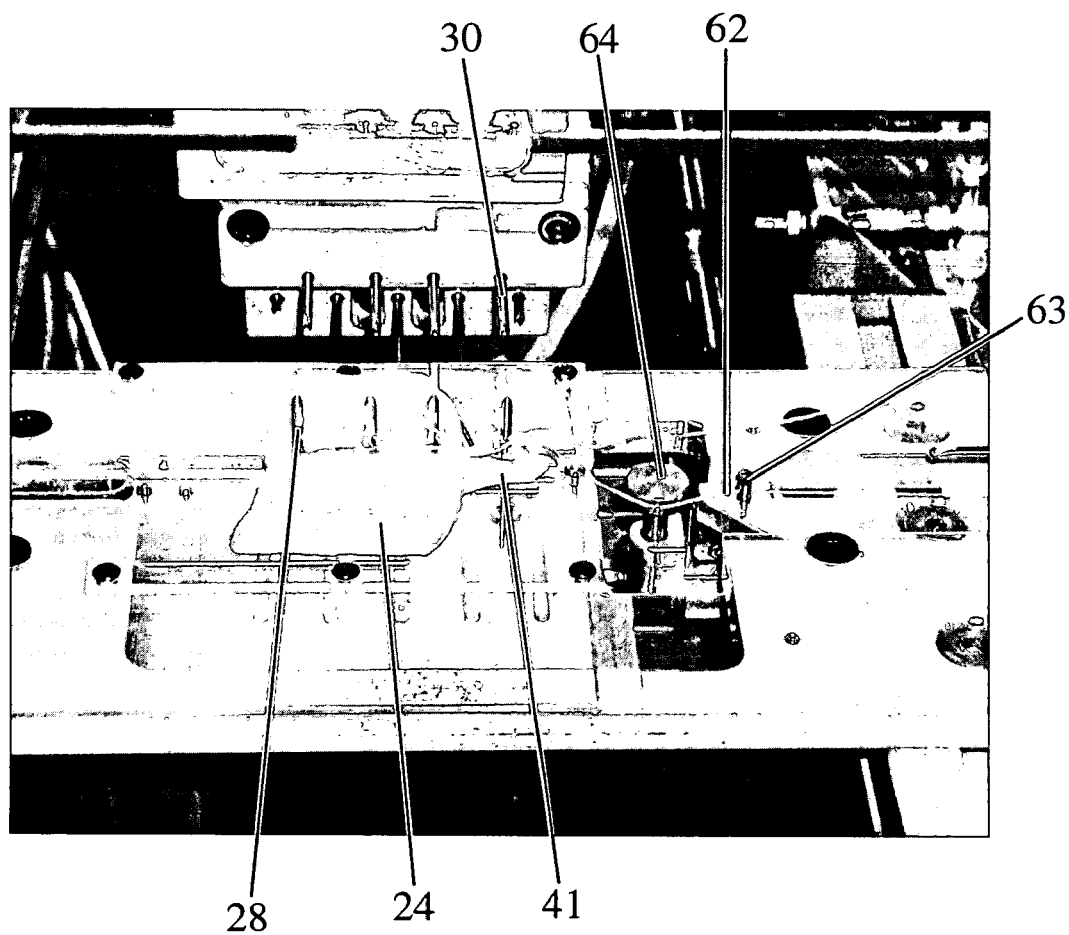
FIG. 8 is a perspective view of the lacing station.
Figure 9:
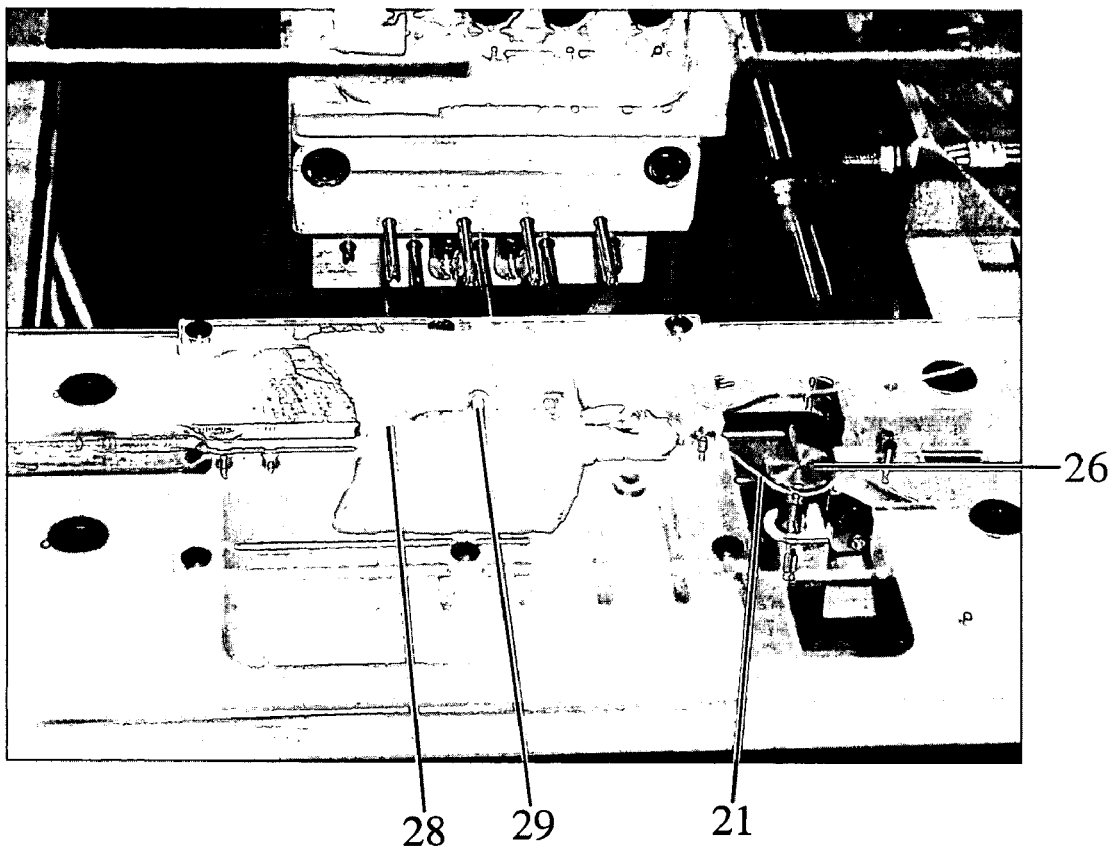
FIG. 9 is a perspective view of the lacing station.

The summarized steps for the method of sewing a cord 21 to a substrate comprise (e.g. tampon pledget) the following steps:

1. Referring to FIG. 1a, place the cord 21 in the groove 22 of plate 74 adjacent to the combers 27.
2. Referring to FIG. 2a, place the pledget 24 on top of the cord 21.
3. Referring to FIG. 3, engage the combers 27 which create slack in the cord 43.
4. Referring to FIG. 4a, retract the combers 27 and penetrate the pledget 24 with the punch pins 28.
5. Referring to FIG. 5a, engage the cord 21 that is looped around the punch pins 28 with the cross pins 30 to create open loops 29.
6. Referring to FIG. 6, thread a portion of the cord 21 through the open loops 29.
7. Referring to FIG. 7, retract the cross pins 30.
8. Referring to FIG. 8, retract the punch pins 28.
9. Referring to FIG. 9, further retract the punch pins 28.

Generally, the method for attaching a cord 21 to a piece of material can be accomplished by employing any combination or sequence chosen from the group of the 3 steps described below. Each step can be repeated continuously, intermittently, concurrently, or steps can be omitted with the only requirement that at least one step is executed at least once during the method of manufacture. The three steps are (1) penetrating the material with the cord 21; (2) forming open loops 29; and (3) threading the cord 21. Again, the sequence and the number of times each step is performed can be any combination as long as each step is performed at least once. Further, sub-steps of each of the steps can be performed in any order or even processed where sub-steps of two different steps are interspersed in time sequence with each other or even done concurrently.

1. Penetrating the Material

As shown in FIG. 3, the penetrating step is used to create openings 33 in the pledget 24 for the cord 21 to enter. The penetrating step creates an opening 33 by changing the modulus in the region of interest to become more capable of allowing the cord 21 to pass through and/or into the pledget 24. The penetrating step can be done at any time after the pledget 24 is placed onto the lacing station (i.e. pre-penetrated pledgets) or while the pledget 24 is placed on the lacing station 23. Referring to FIG. 4a, the penetrating step can be done singly or multiple times before forming the open loops 29. Notably, the cord 21 may be in contact with the pledget 24 before the punch pins 28 penetrate the pledget 24. Moreover, the cord 21 is stationary and pre-positioned relative to the punch pins 28 before penetration of the pledget 24.

The penetrating step can be accomplished by any known means though preferably they are either mechanical and/or chemical. Using a punch pin 28 to penetrate the material is an example of a mechanical penetrating means.

Figure 4B:
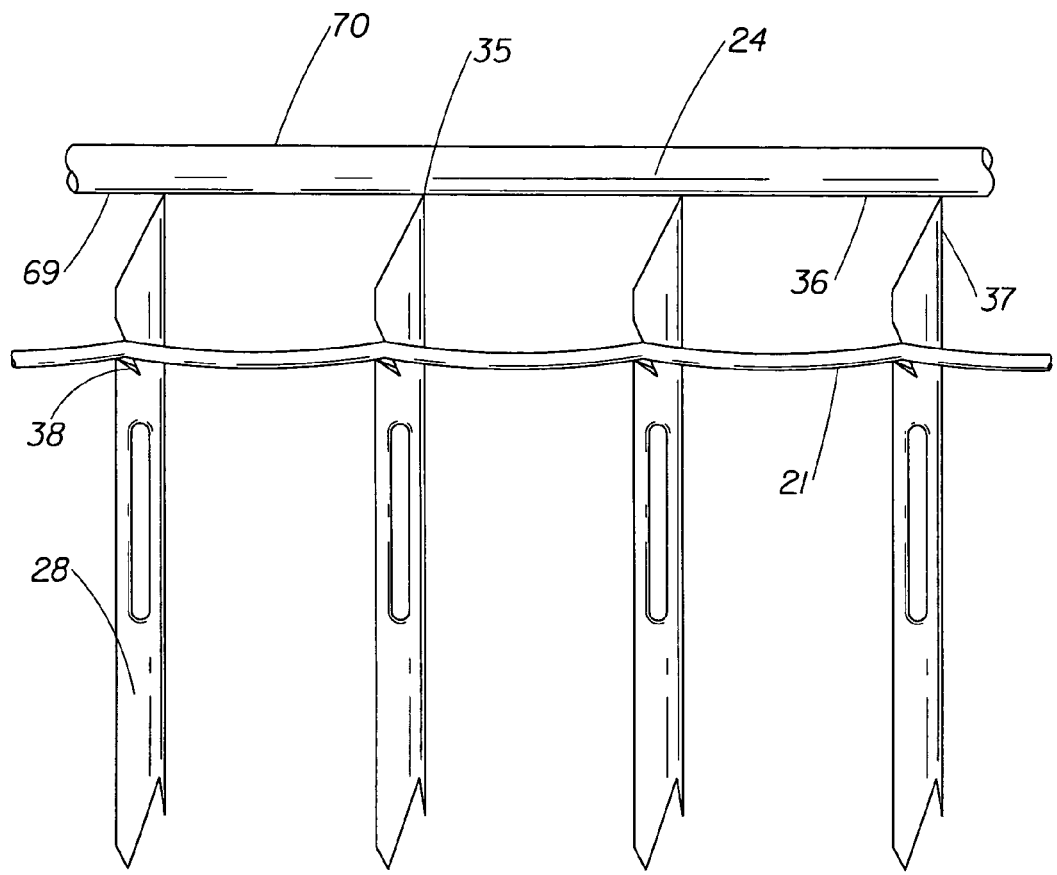
FIG. 4b is a perspective view of the punch pins.
Figure 5B:
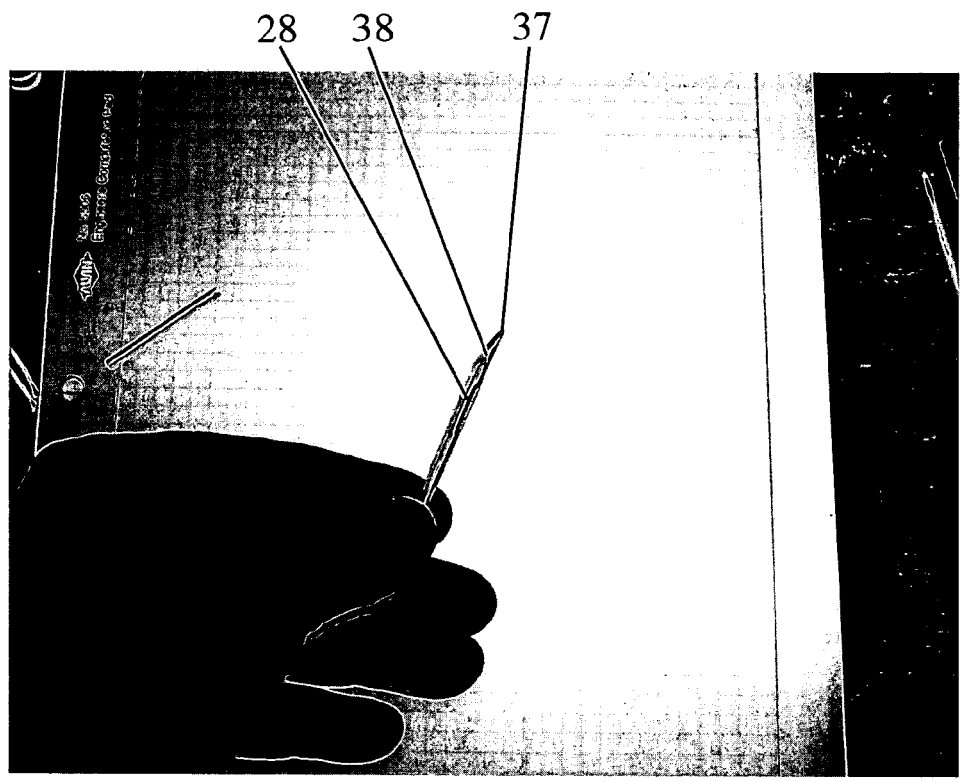
FIG. 5b is a perspective view of a punch pin.

Referring to FIG. 4b, the punch pin 28 is a type of needle. There is significant variety in the size and shape of available and usable punch pins 28. The proposed invention is functional with a wide variety of these and for the purpose of this document, should not be limited to any particular punch pin 28 embodiment, so long as the point 37 of the punch pin at the point of entry into the pledget 24 is sufficient to penetrate the pledget 24. In other words, the punch pin 28 can be any shape as desired as long as the punch pin 28 has a point 37 which can penetrate the pledget 24. The shape of the punch pin 28 can be cylindrical so that it comes to a point 37 for easy penetration into the pledget, fabric or garment. In one embodiment, as seen in FIG. 5b, the point 37 of the punch pin 28 is angled. The angle 37 decreases the punch force as the punch pin 28 penetrates the pledget 24. In addition, the angle 37 draws less material through the pledget 24. In another embodiment, the point 37 of the punch pin 28 has a conical shape. While the main body of the punch pin 28 typically is a cylinder with a circular cross section, other cross sections are possible such as flat, rectangular, square, elliptical, polygonal, triangular, etc. The material of the punch pin 28 is often comprised of a metal or rigid polymer composition.

Referring to FIG. 4b, the punch pins 28 may have a groove 38 to hold at least a portion of the cord 21. The groove 38 can be any shape and placed on any location on the punch pin 28 as long as the groove 38 is shaped to secure the cord 21 during the penetrating step long enough to allow the cord 21 to travel from the first side 69 of the pledget 24 to the second side 70 of the pledget 24. In one embodiment, as shown in FIG. 4b, the groove is facing the combers 27.

Any number of punch pins 28 may be utilized. Either an even or an odd number of punch pins 28 can be present and the punch pins 28 can be equally spaced apart or they can be non-uniformly arranged. Uniformly arranged punch pins 28 are preferred but randomly arranged punch pins 28 will work. For ease of manufacturing, it is preferred that the punch pins 28 be equally spaced relative to one another.

Another penetrating technique involves chemical softening such as the addition of any agent that at least partially inhibits, disrupts or displaces the formation of bonds between fibers, e.g. hydrogen bonds. Not to be bound by any theory, but at least two mechanisms can be used: 1) impregnate the area of the pledget 24 in which the cord 21 will penetrate with a liquid that itself forms hydrogen bonds with the fibers (thus reducing the number of hydrogen bonds between fibers) or 2) impregnate the pledget 24 with a low-polarity solvent, that causes weakening of the bonds between fibers due to its dielectric constant. Some examples of possible hydrogen bond disruption, inhibition, or weakening agents include the addition of water, aqueous solutions, glycerol, polyethylene glycol, other glycols, chemicals exhibiting hydroxyl or amine functionalities, or chemicals with sulphur-containing groups.

In addition, the liquid blast technique is another penetrating technique. This technique uses liquid at high pressures to penetrate the pledget 24 which creates openings 33. Typically a pump is connected to the liquid source, and is adapted to supply the liquid at a desired volume and high pressure to an inlet of the nozzle. Typically, the pump is capable of pressure up to 10,000 pounds per square inch ("psi") and flow rates up to 5 gallons per minute ("gpm"). Any type of liquid may be used. Typically, water is used to create the blast.

Referring to FIG. 3, the pledget 24 could be penetrated in tandem with the cord 21 going through the pledget 24.

Alternatively, the cord 21 could go through the opening 33 after the opening 33 is formed.

2. Forming Open Loops

Referring to FIG. 5a, after the pledget 24 is penetrated, the cord 21 forms open loops 29 with any device or a combination of devices. The open loops 29 should be large enough to provide sufficient space for the spear 31 to travel through each open loop 29.

Figure 4C:
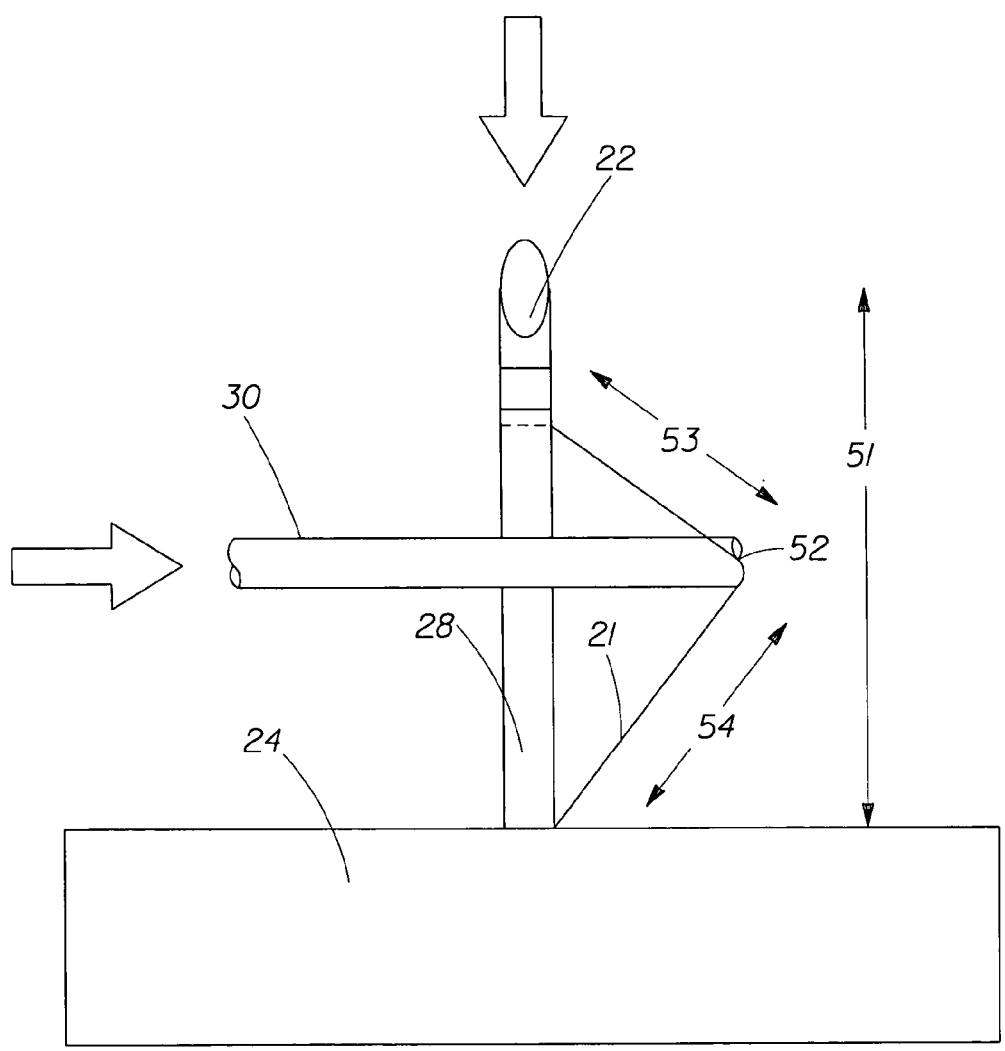
FIG. 4c is a perspective view of the punch pins and combers.
Figure 4D:
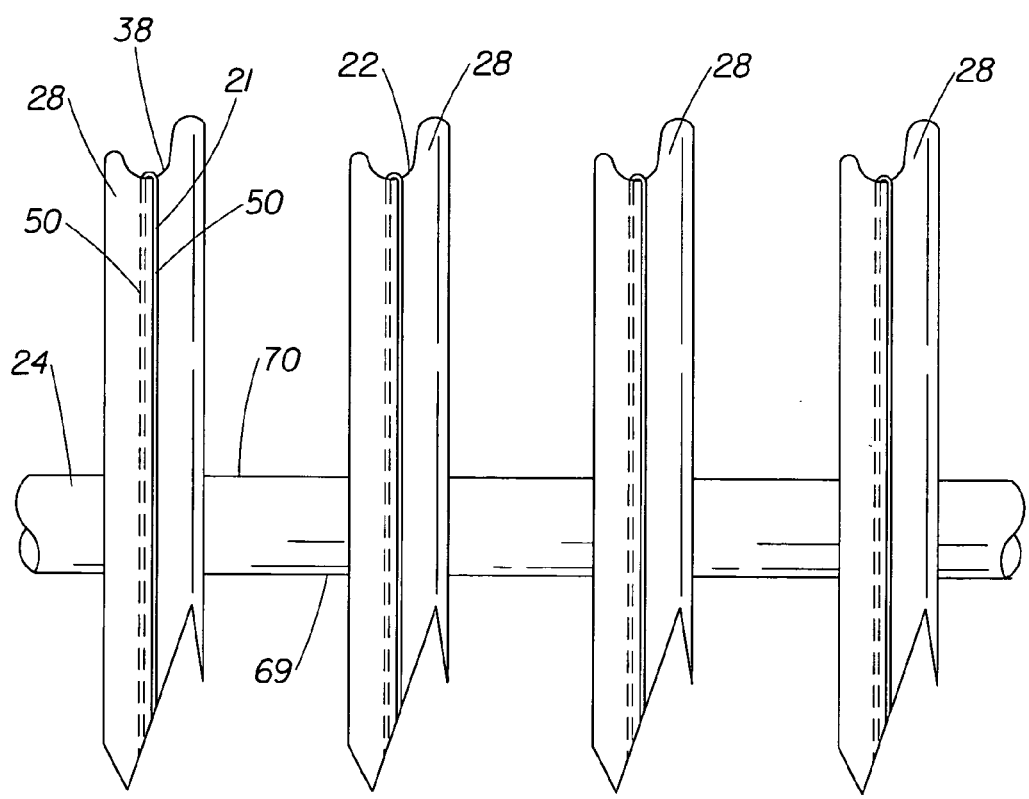
FIG. 4d is a perspective view of the punch pins.
Figure 4E:
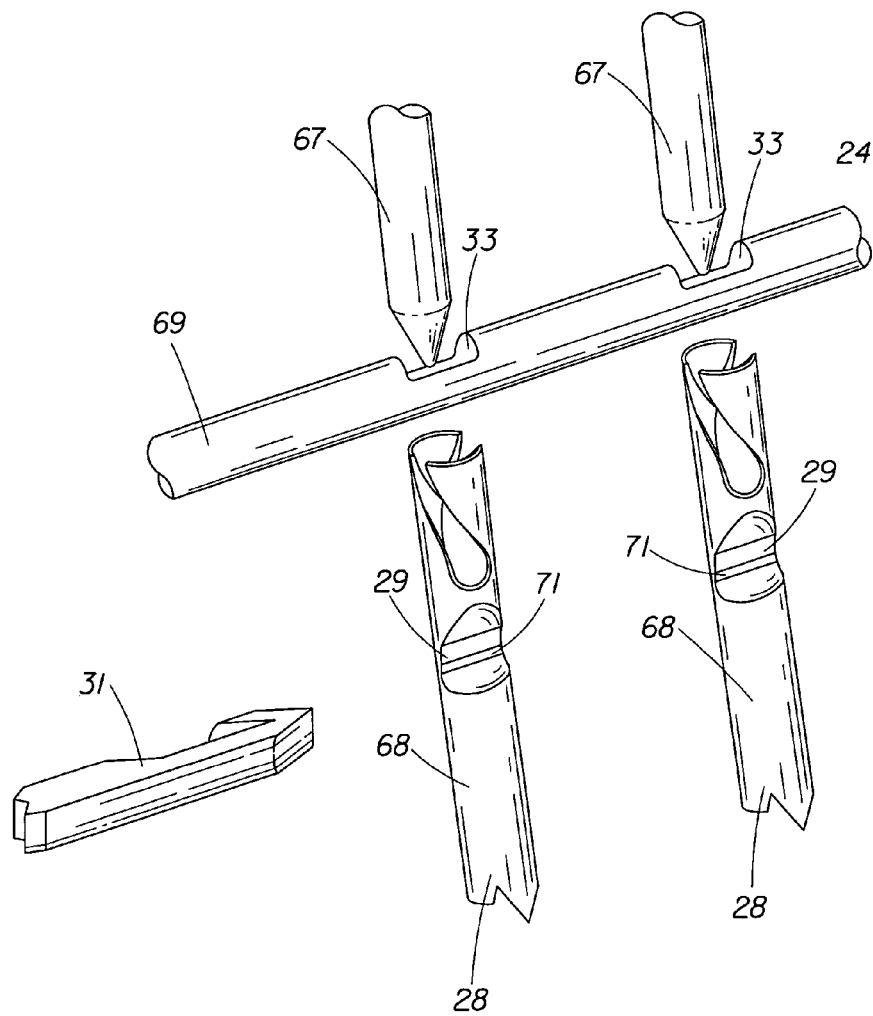
FIG. 4e is a perspective view of an alternative embodiment of the punch pins.

Referring to FIG. 4d, the shape of the punch pins 28 may create open loops 29 on one side of the pledget 24. As shown in FIG. 4e, in one embodiment, the shape of the punch pin 28 creates open loops 29 for the spear 31 to travel through the open loops 29. In this embodiment, a first member 67 penetrates a first side 69 of the pledget 24 and travels to a second side 70 of the pledget 24 to create an opening 33 and to mate with a second member 68. Next, both the first member 67 and the second member 68 go through the second side 70 of the pledget 24 to the first side 69 of the pledget to form open loops 29 on the first side 69 of the pledget 24. The spear 31 then travels through the indentation 71 of the punch pin 28. The spear 31 passes through the indention 71 but catches a portion of the cord 21 of the last open 29 and pulls the last open loop 29 through the other indentions 71.

As shown in FIG. 5a, alternatively an open loop 29 can be formed or made wider using a punch pin 28 and a cross pin 30. During penetration of the pledget 24 by the punch pins 28, the cord 21 rests inside of the groove 38 of the punch pin 28. After penetration of the punch pin 28 through the pledget 24, the groove 38 of the punch pin 28 holding the cord 21 is placed above the pledget 24. After the punch pins 28 penetrate the pledget 24, the cross pins 30 engage a portion of cord 21 to form open loops 29. In one embodiment, the cross pin 30 which creates the last open loop 32 travels a farther distance than the rest of the cross pins 30. This makes a larger open loop 32. There are several advantages to this embodiment. First, by creating open loops 29 above the pledget 24, the openings 33 in the pledget 24 are only as large as the diameter of the punch pin 28 that penetrates the pledget 24 to push the cord 21 through the pledget 24. Smaller openings 33 are more desirable to create a more attractive consumer product. In addition, smaller openings 33 create better cord 21 attachment by providing more continuous material which results in the cord 21 having better anchor strength to the pledget 24. Second, there are two main parts to this embodiment—the punch pins 28 and the cross pins 30. By having minimum parts to construct the open loops 29, there is more reliability and a lower cost. Third, this embodiment creates flexibility in making the open loops 29 larger using the cross pins 30 without adversely affecting the openings 33 in the pledget 24.

As shown in FIG. 4c, the combination of the cross pins 30 and the punch pins 28 form a triangular window with the cord 21. A first portion 51 of the cord 21 extends up through the pledget 24 to the groove 22 of the punch pin 28. A second portion 53 extends from the groove 22 of the punch pin 28 out to the groove 52 of the cross pin 30. A third portion 54 of the cord 21 extends from groove 52 of the cross pin 30 down through the pledget 24.

Any number of cross pins 30 may be utilized to form open loops 29. Typically, there is at least one cross pin 30 for each punch pin 28. Either an even or an odd number of cross pins 30 can be present and the cross pins 30 can be equally spaced apart or they can be non-uniformly arranged. Uniformly arranged cross pins 30 are preferred but randomly arranged cross pins 30 will work so long as the cross pins 30 do not interfere mechanically with the path of the punch pins 28. For ease of manufacturing, it is preferred that the cross pins 30 be equally spaced relative to one another.

In one embodiment, the pledget 24 has pre-formed openings 33. In this case, the cord 21 is drawn through existing openings 33 and the open loops 20 are formed on the second side 70 of the pledget 24. In an alternative embodiment, the step to form open loops 29 can be accomplished by using punch pins 28 to push the cord 21 through a first side 69 just far enough for the cord 21 to extend to the second side 70.

3. Threading the Cord

Referring to FIG. 6, the cord 21 is secured to the pledget 24 by threading a portion of the cord 21 through open loops 29. A portion of the cord 21 must be threaded through the open loops 29 by any known means in the art. A portion of the cord 21 must go through one open loop 29 or many open loops 29. Also, the cord 21 may go through each open loop 29 continuously, intermittently, or one or more open loops 29 can be omitted with the only requirement that at least a portion of the cord 21 enter at least one open loop 29. In one embodiment, the cord 21 comprises secondary absorbent which is also threaded through one or more open loops 29.

The cord 21 may follow or outline any path, e.g. straight or circuitous, before, after or in-between threading the loop(s). The cord 21 may be in partial, full, limited, or in no contact with the material before, during, or after threading the cord 21 loop. The cord 21 path may follow or parallel the surface of the material, partially or fully circumscribe the material whether in material contact or not, or may partially or fully penetrate the material. The cord 21 may intersect or overlap itself to or from a threaded loop or between threaded loops.

Any device can be used to thread a portion of the cord 21 through an open loop 29. Referring to FIG. 5a, a spear 31 can be used to thread a portion of the cord 21 through an open loop 29. Referring to FIG. 6, a spear 31 may be mounted anywhere on the lacing station 23. The spear 31 could be stationary, moveable, placed on a drum, or placed on an overhead support clamp 48. Referring to FIG. 1a, specifically, the spear 31 may be mounted to the overhead support clamp 48. In this embodiment, the spear 31 is movably connected to the lacing station 23. Referring to FIG. 5a, in one embodiment, after the cord 21 forms the triangle with the cross pins 30 and the punch pins 28, the spear 31 is actuated.

The spear 31 can be follow any movement path. The path of movement could be linear or nonlinear. In addition, the spear 31 can travel in one direction or more than one direction. In one embodiment, the spear 31 travels in two directions to complete the threading step. Referring to FIG. 5a, in this embodiment, the cross pin 30 which engages the last open loop 32 travels a shorter distance in the Y direction 65 than the rest of the cross pins 30. Because the first cross pin 56 travels a shorter distance, the last open loop 32 does not have as large of an open loop. This allows the spear 31 to pass the last open loop 32 when traveling in a first direction 57, but allows the spear 31 to engage the last open loop 32 when traveling in a second direction 58. Specifically, on the return stroke of the spear 31, the curved hook 49 of the spear 31 grabs the cord 21 of the last open loop 32 and pulls it through the other open loops 29. Alternatively, the last open loop 32 could be formed outside of the pledget 24 or without the use of punch pins 28 or cross pins 30. The spear 31 would act in the same manner which is engaging the last open loop 32 and pulling it though one or more of the remaining open loops 29.

C. High Speed Manufacturing Process

Figure 1B:
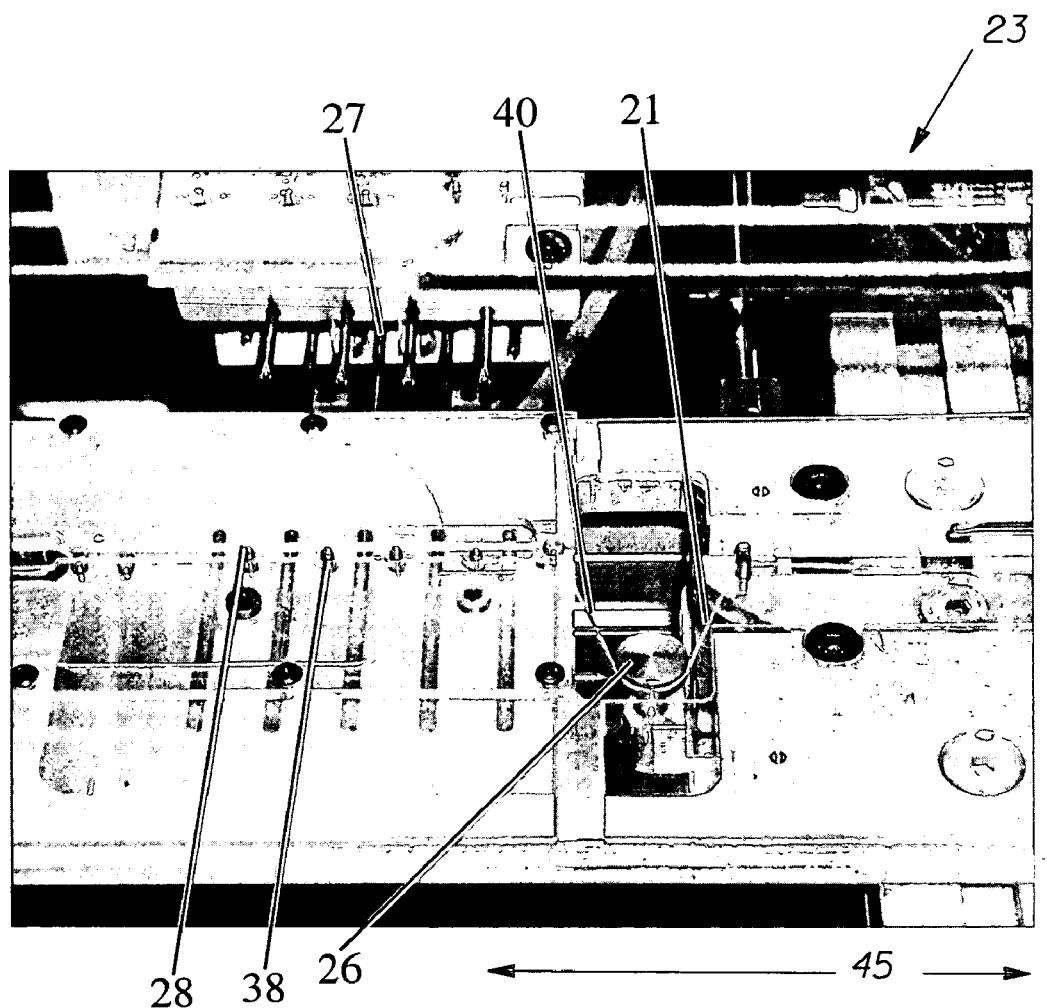
FIG. 1b is a perspective view of the lacing station.
Figure 2B:
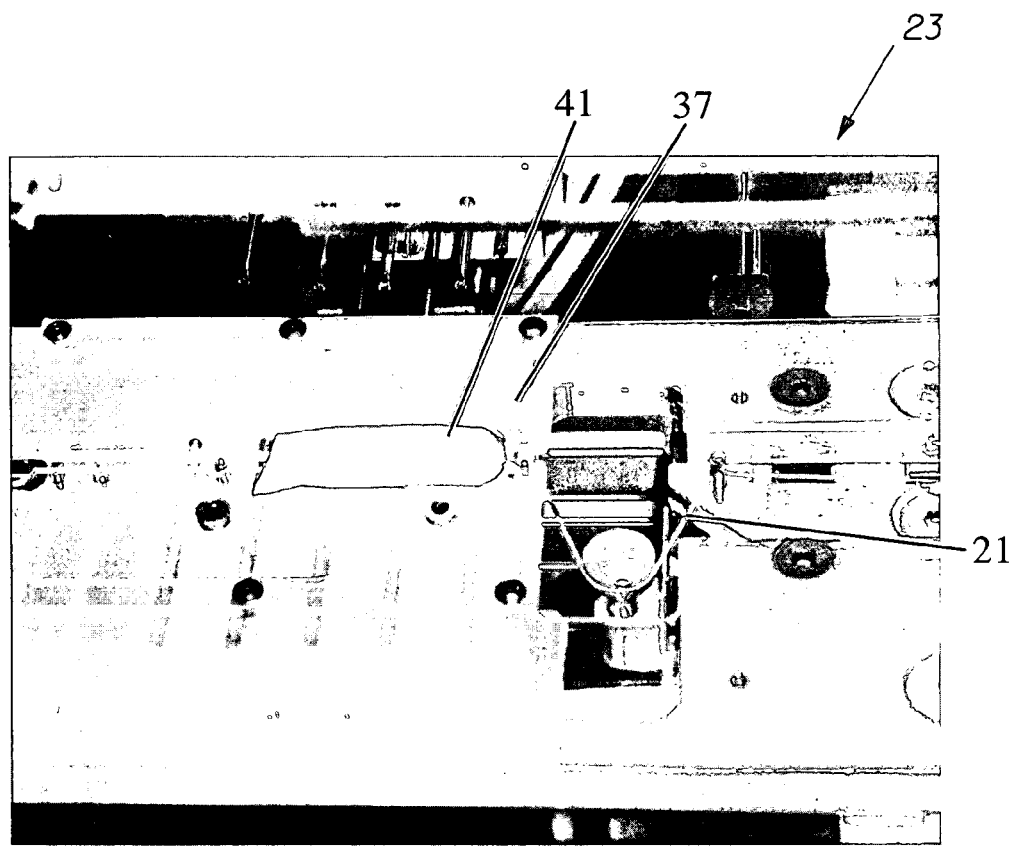
FIG. 2b is a perspective view of the lacing station.
Figure 2C:
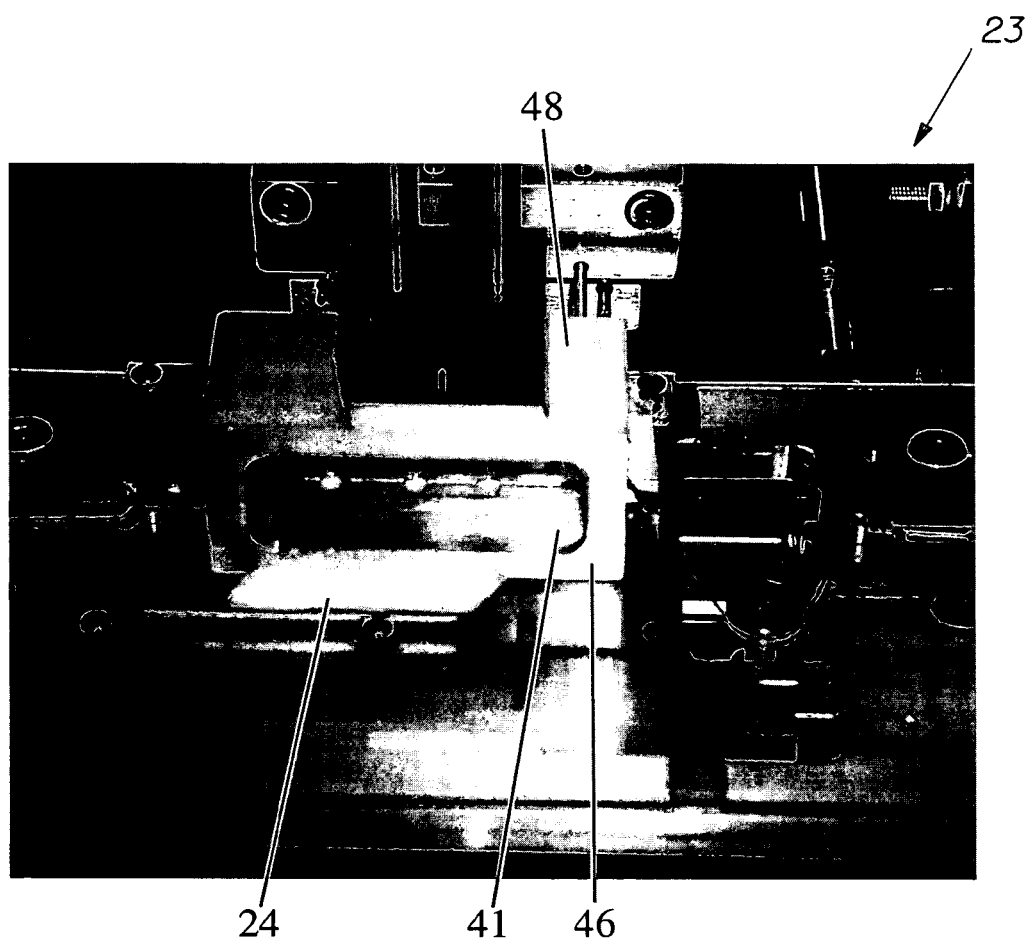
FIG. 2c is a perspective view of the lacing station.
Figure 2D:
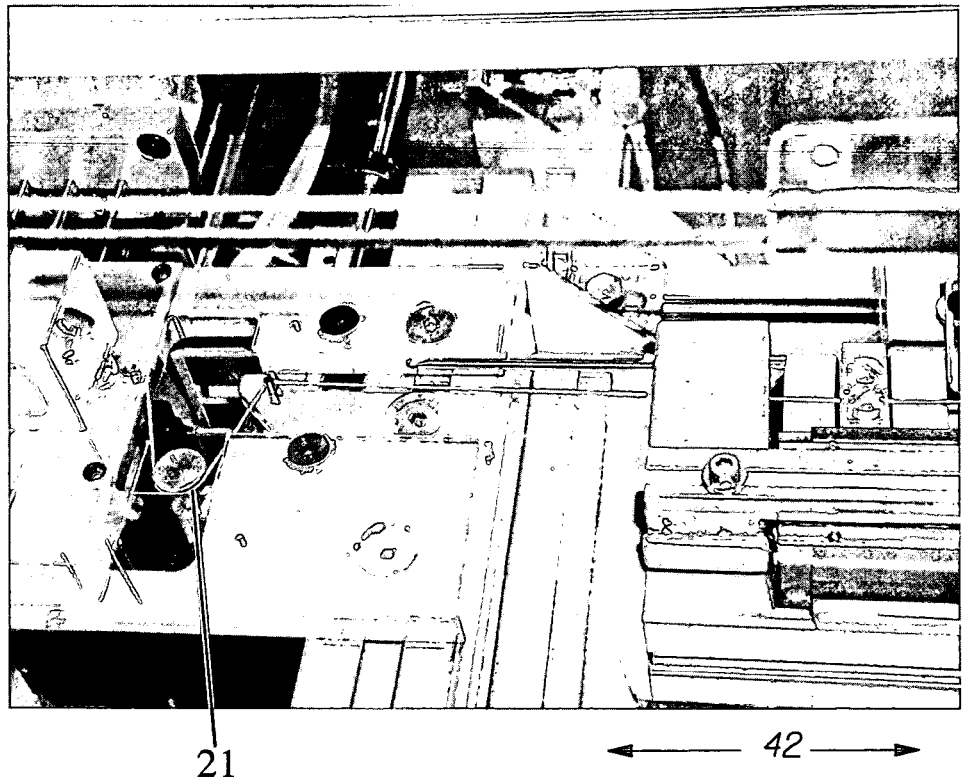
FIG. 2d is a perspective view of the lacing station.
Figure 2E:
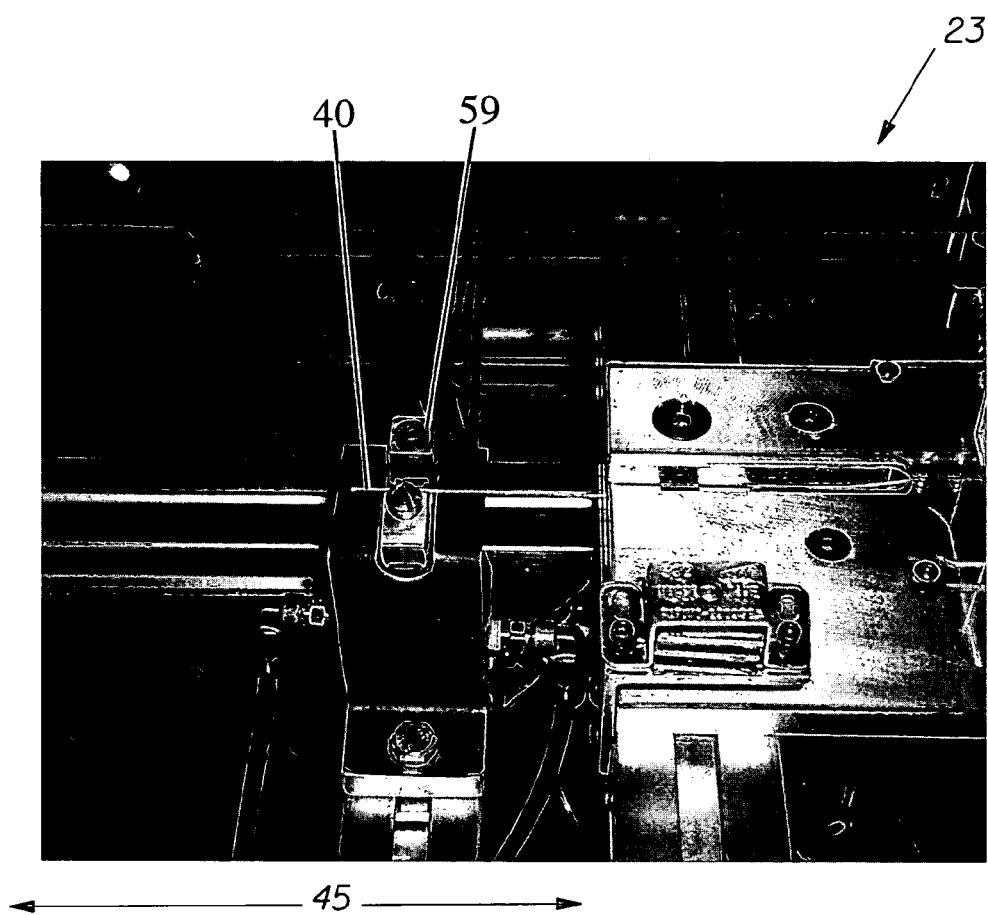
FIG. 2e is a perspective view of the lacing station.
Figure 10:
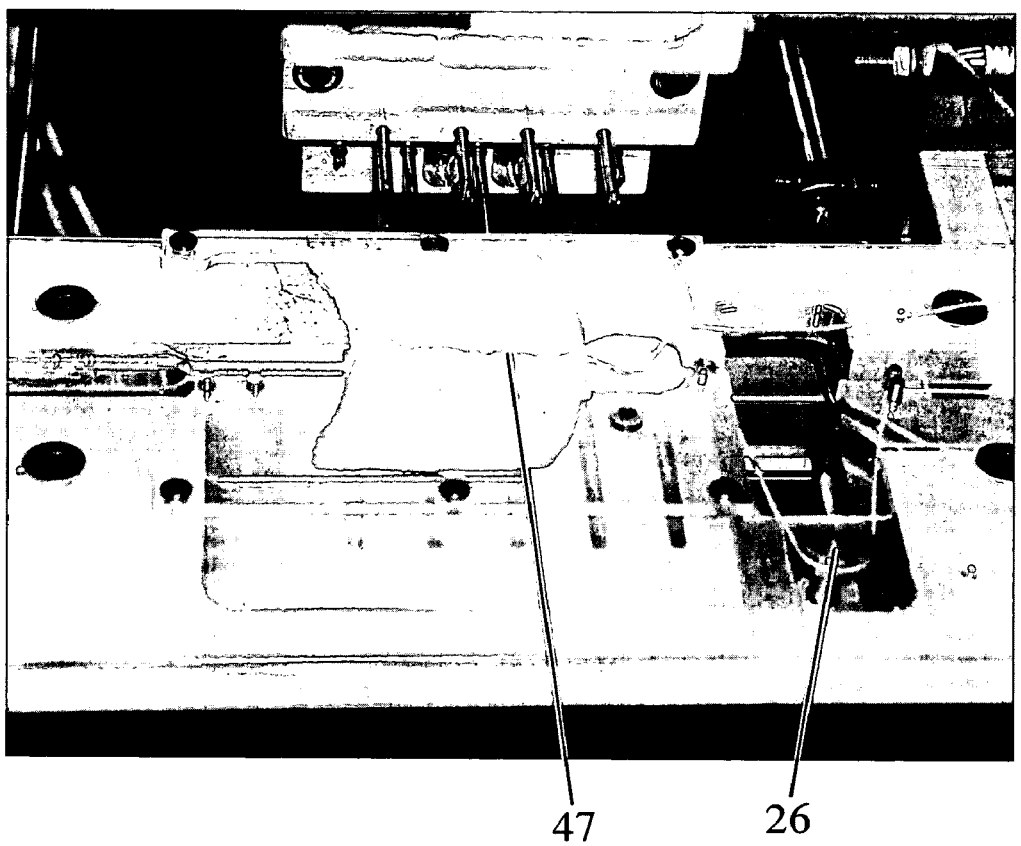
FIG. 10 is a perspective view of the lacing station.
Figure 11:
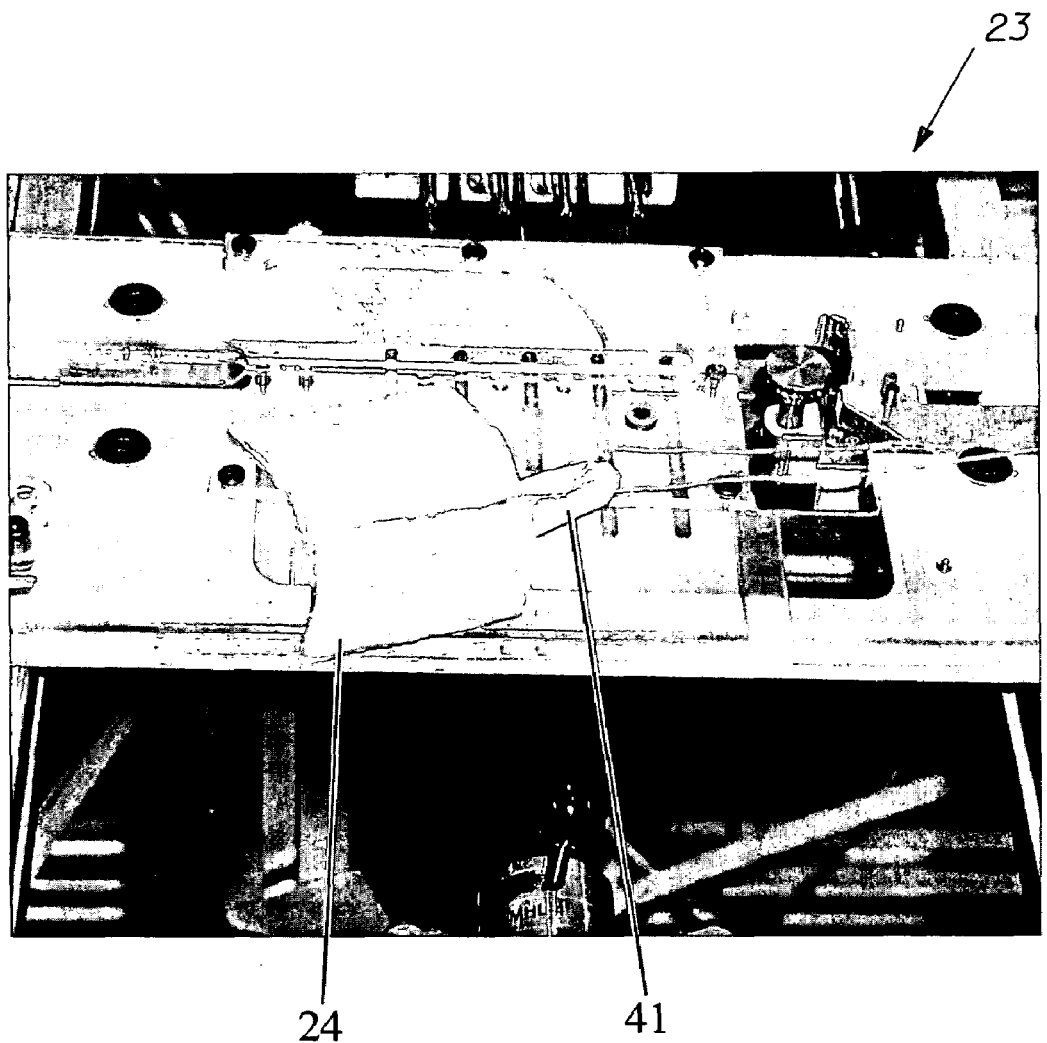
FIG. 11 is a perspective view of the lacing station.

The following is an example of a high speed process of attaching a cord 21 to a pledget 24. This is an example which is not limited to the below example. Changes could be made to the process without departing from the spirit and scope of the invention. The summarized steps for the method of sewing a cord 21 to a substrate comprise (e.g. tampon pledget 24) the following steps:

1. Referring to FIG. 1a, place the cord 21 in the groove 22 adjacent to the combers 27 of the lacing station 23.
2. Referring to FIG. 1a, clamp the downstream end 40 of the cord 21.
3. Referring to FIG. 1b, draw the cord 21 into the upstream side 45 of the lacing station 23 with the upstream festoon idler 26.
4. Referring to FIG. 2b, place the secondary absorbent 41 onto the surface 37 of the lacing station 23 and thus onto the cord 21.
5. Referring to FIG. 2a, place the pledget 24 next to the secondary absorbent 41 and onto the cord 21.
6. Referring to FIG. 2c, support the secondary absorbent 41 and pledget 24 with a supporter 46 to hold the secondary absorbent 41 and the pledget 24 in place for processing.
7. Referring to FIG. 2d, clamp the upstream end of the cord 42, thus fixing the length of the cord 21 in an individual station.
8. Referring to FIG. 2e, cut the downstream end of cord 40 with the downstream clamp 59 which is located on the downstream end 45 of the lacing station 23 which allows the downstream end of the cord 40 to go freely.
9. Referring to FIG. 3, retract the upstream festoon idler 26 while pulling the slack cord 43 under the surface of the lacing station 23 with combers 27. During this stage, the cord 21 is loaded into the punch pins 28 by the motion of the combers 27.
10. Referring to FIG. 4a, retract the combers 27 to create slack in the cord 43 as the punch pins 28 penetrate the pledget 24 and the secondary absorbent 41.
11. Referring to FIG. 5a, engage cross pins 30 to create open loops 29 above the pledget 24.
12. Referring to FIG. 6, thread the last open loop 32 through one or more other open loops 29.
13. Referring to FIG. 7, retract the cross pins 30.
14. Referring to FIG. 8, begin retracting punch pins 28.
15. Referring to FIG. 9, retract punch pins 28 leaving open loops 29 remaining.
16. Referring to FIG. 10, create cinched loops 47 with upstream festoon idler 26.
17. Referring to FIG. 11, remove laced pledget 24 and secondary absorbent 41 from lacing station 23.

Figure 12:
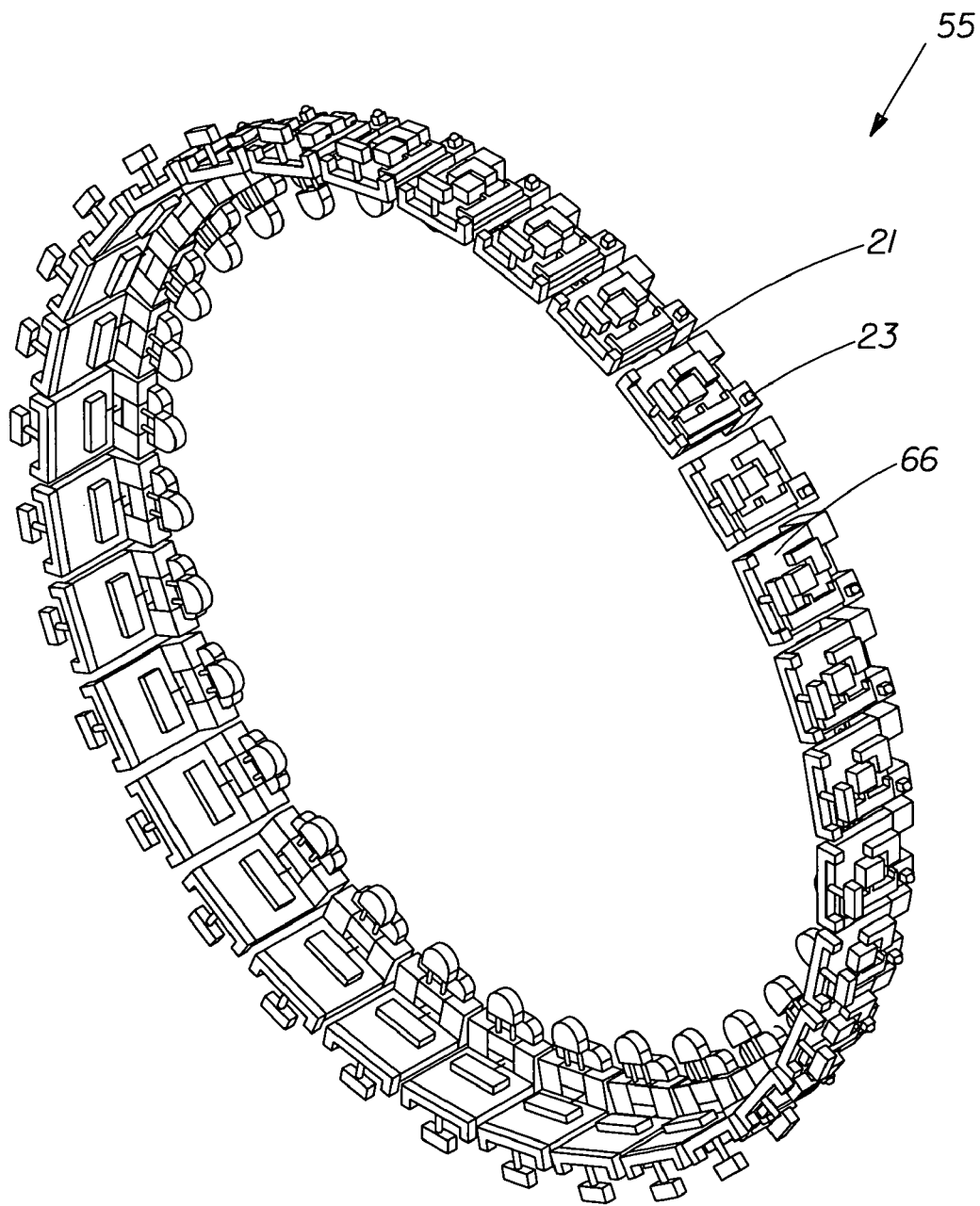
FIG. 12 is a perspective view of several lacing stations.

Referring to FIG. 12, this process can create a high speed manufacturing process using a drum 55, chain, or any other known means in the art with individual lacing stations 23. Specifically, a plurality of lacing stations 23 are used to achieve high-speed assembly of a tampon. Each individual lacing station 23 may perform the same function, as described above, simultaneously.

A drum 55 may contain any number of lacing stations 23. Either an even or an odd number of lacing stations 23 can be present and the lacing stations 23 can be equally spaced apart or they can be non-uniformly arranged. Uniformly arranged lacing stations 23 are preferred but randomly arranged lacing stations 23 will work. For ease of manufacturing, it is preferred that the lacing stations 23 be equally spaced relative to one another.

Referring to FIG. 1a, to perform a high speed manufacturing process, initially the cord 21 is fed into the lacing station 23. Referring to FIG. 12, in one embodiment, the cord 21 is fed from the side 66 of the lacing station 23. The cord 21 is fed from the side 66 to insure that the cord 21 is in-line with the lacing stations 23 as they are moving around the drum 55.

In one embodiment, as shown in FIG. 1a, the cord 21 sits in a groove 22 below the surface of the lacing station 23. The downstream end of the cord 40 is clamped by a damper 25. Typically, an upstream cord festooning idler 26 and a downstream cord festooning idler 26 (not shown) are actuated to pull the proper amount of cord 21 into the system. The cord damper 25 for the next lacing station 23 clamps the upstream end of the cord 42. At this point in the process, all the cord 21 for the individual product has been metered into the lacing station 23 and the ends are isolated.

Referring to FIG. 2e, the downstream end of the cord 40 is cut as the festoon idlers 26 (FIG. 3) retract towards their original position (FIG. 1a). As shown in FIG. 3, as this is happening, the combers 27 pull the loose cord into the lacing station 23 below the surface. When the combers 27 are actuated, they pull the cord 21 around the punch pins 28. As a result, the combers 27 load the cord 21 into the groove 38 of the punch pins 28.

Figure 2F:
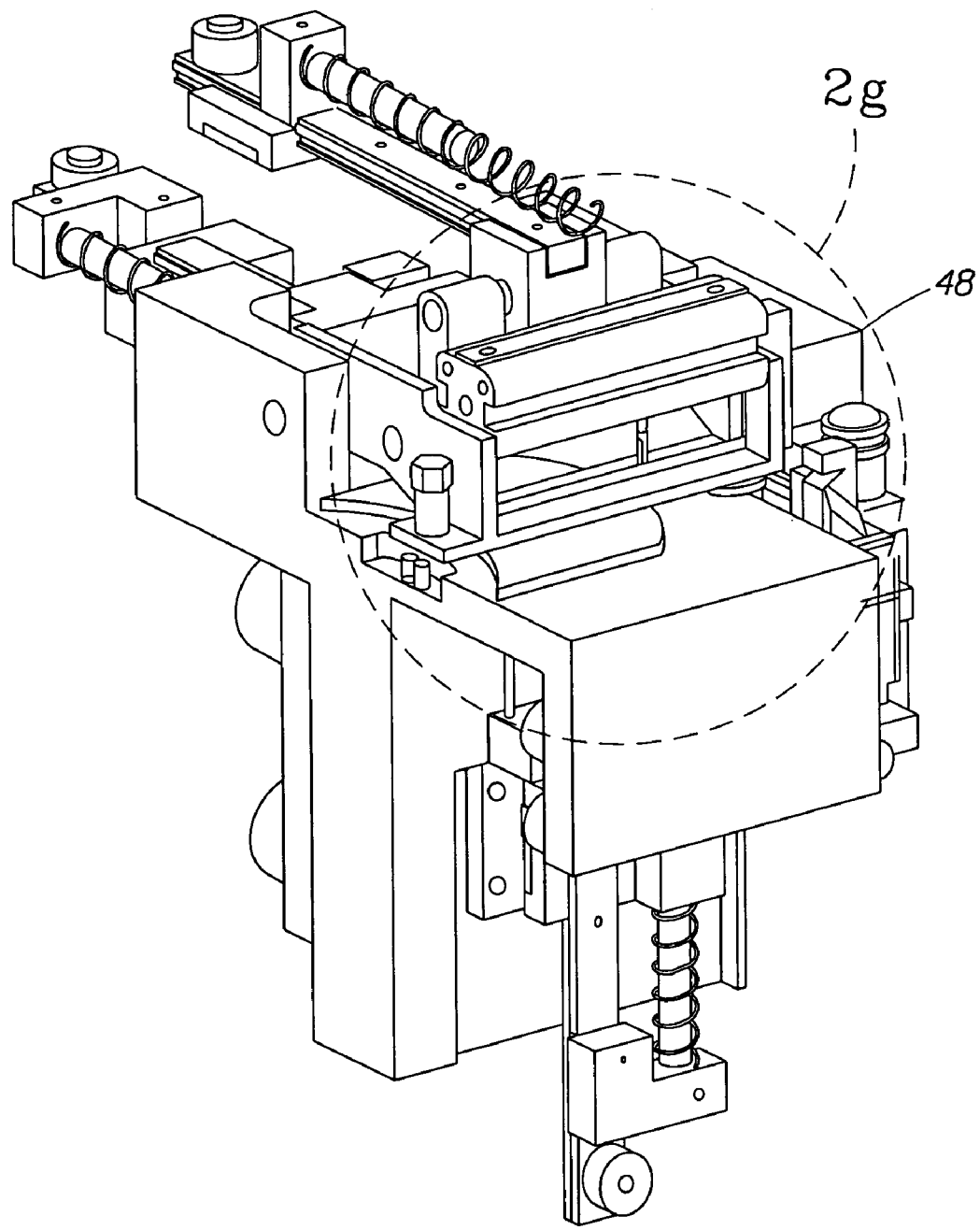
FIG. 2f is a perspective view of the lacing station.
Figure 2G:
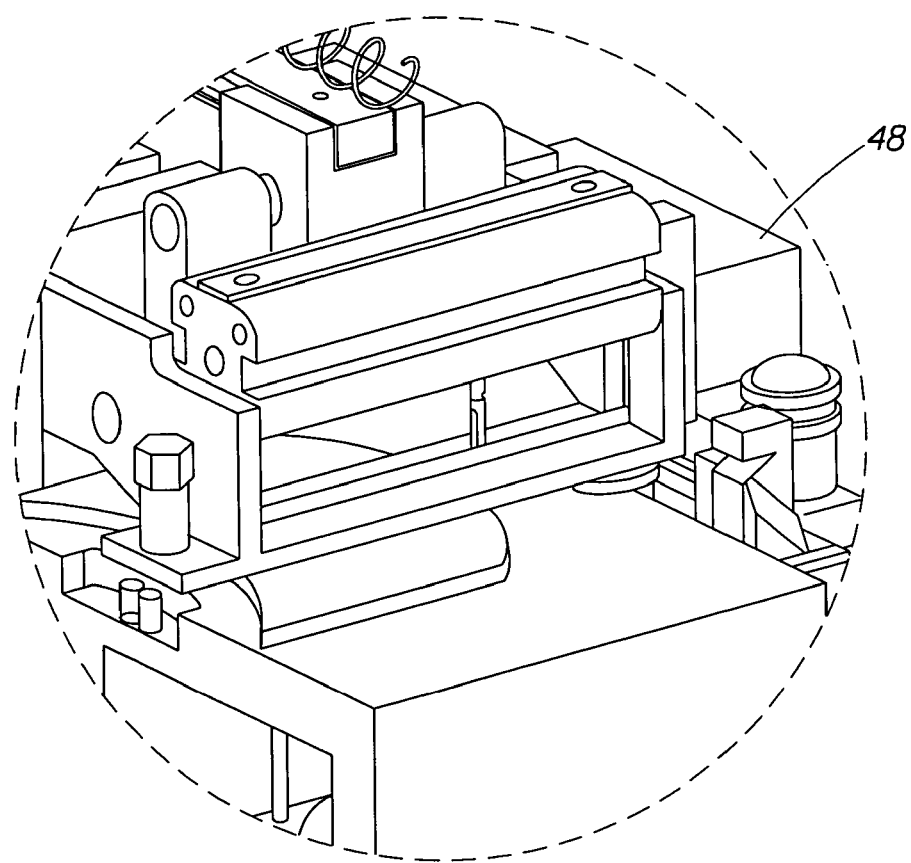
FIG. 2g is a perspective view of the lacing station.

Referring to FIG. 2b, while the above steps are taking place with the cord 21, a secondary absorbent 41 is laid down on the top surface of the lacing station 23 and held in place with a vacuum or by any known means in the art. Referring to FIG. 2b, a tampon pledget 24 is then laid on top of the secondary absorbent 41 and held in place by a vacuum or by any known means in the art. Referring to FIG. 2c, after the materials are laid down on the lacing station 23, an overhead support block 48 clamps the pledget 24 and the secondary absorbent 41 to the lacing station 23. The overhead support block 48 can be used throughout the entire process. Essentially, the process can work through the overhead support block 48. The overhead support block 48 holds down the pledget 24 and/or the secondary absorbent 41 throughout the entire process. This is important for the pledget 24 to maintain its placement. More importantly, the overhead support block 48 holds down the pledget 24 and/or secondary absorbent 41 while the punch pins 28 penetrate the pledget 24 and while the pledget 24 is being cinched. Thus, the overhead support block 48 holds down the pledget 24 and/or the secondary absorbent 41 while any amount of force is being placed on the pledget 24. FIG. 2f shows an alternative embodiment of the overhead support block 48. FIG. 2g shows a close up view of the overhead support block 48.

Referring to FIG. 4a, next, four punch pins 28 punch the cord 21 through the secondary absorbent 41 and the pledget 24. As shown in FIG. 4d, this forms a loop of cord 21 that extends from the first side 69 of the pledget 24 up through to the second side 70, around the groove 38 of the punch pins 28, and back down through the pledget 24 to the first side 69. As shown in FIG. 4a, as the punch pins 28 start punching through the product, the combers 27 return to their initial position. These two events are timed such that the combers 27 release the cord 21 just as the punch pins 28 start moving up.

As shown in FIG. 5a, after the punch pins 28 penetrate the pledget 24, the cross pins 30 engage a portion of cord 21. Referring to FIG. 4d, in one embodiment, the cross pin 30 engages the side 50 of the cord 21 which is looped around the corresponding punch pin 28. As shown in FIG. 4c, this forms a triangular window with the cord 21. A first portion 51 of the cord 21 extends up through the pledget 24 to the groove 22 of the punch pin 28. A second portion 53 extends from the groove 22 of the punch pin 28 out to the groove 52 of the cross pin 30. A third portion 54 of the cord 21 extends from the groove 52 of the cross pin 30 down through the pledget 24.

Referring to FIG. 6, after the cross pins 30 form the open loops 29 above the pledget 24 and the secondary absorbent 41, the spear 31 is actuated. The spear 31 passes through the open loops 29 but does not pass through the last open loop 32 when traveling in a first direction 57. In one embodiment, when the spear 31 is actuated and traveling in a first direction the spear 31 extends beyond the last open loop 32. The spear 31, however, on the return stroke which is traveling in a second direction 58 engages a portion of the last open loop 32 when traveling in a second direction 58. Specifically, on the return stroke of the spear 31, the curved hook 49 of the spear 31 grabs at least a portion of the last open loop 32 and pulls it through the other open loops 29.

Referring to FIG. 5 the spear 31 extends out through the inside part of the first three open loops 29 of cord 21, but moves past the last open loop 32. In other words, the spear 31 does not enter into the last open loop 32, but actually remains outside of it. On the return stroke of the spear 31, the curved hook 49 of the spear 31 grabs a portion of the last open loop 32 and pulls it through the other open loops 29.

In an alternative embodiment, the spear is actuated in a first direction. The spear 31 grabs a portion of the last open loop 32 that it crosses and pulls it through the other open loops 29 without returning in the opposite direction. In another alternative embodiment, the spear 31 grabs a portion of the last open loop 32 and returns in the opposite direction to began the process again with another pledget 24.

Referring to FIG. 7, after a portion of cord 21 is pulled through the other open loops 29, the cross pins 30 return to their original positions and the punch pins 28 retract through the pledget 24. Referring to FIG. 8, at this point the upstream end of the cord 62 is still being held by the cord cutter/clamp 63. The end of cord 21 has been cut during the processing of the next lacing station 23 (not shown), however the end of cord 21 remains held in place by the cord clamp 63. The upstream festoon idler 64 is actuated and cinches the cord 21 in place by pulling the loose cord that had formed the open loops 29. Referring to FIG. 11, the upstream end of the cord 62 is released and the laced pledget is removed from the lacing station 23.

Referring to FIG. 2a, in other alternative embodiments, the secondary absorbent 41 can be combined with the pledget 24 before the manufacturing process, concurrently with the manufacturing process, or after the manufacturing process. In other words, the secondary absorbent 41, a composite component of the material being punched, or the secondary absorbent 41 can be concurrently and/or jointly attached to the pledget 24 as part of the cord attachment process. Alternatively, the secondary material 41 can be associated with or even attached to the cord 21. In this embodiment, the secondary absorbent 41 may even have portions threaded through one or more open loops 29.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of attaching a cord to a piece of material which comprises:
   a) providing a cord;
   b) providing a material having a first side and a second side;
   c) providing a comber;
   d) providing a punch pin with a first end and a second end;
   e) providing a spear;
   f) providing a cross pin;
   g) placing a cord on a surface;
   h) placing said second side of said material on top of said cord;
   i) moving said comber in a first direction which creates slack in said cord by engaging said cord with said comber;
   j) penetrating said material with a portion of said cord and said second end of said punch pin to form an open loop at said first side of said material with said punch pin;
   k) maintaining said open loop with said cross pin; and
   l) passing a portion of said cord through said open loop with said spear.

2. Apparatus for attaching a cord to a piece of material having a first side and a second side which comprises:
   a) a frame;
   b) a punch pin;
   c) a spear;
   d) a comber;
   e) said comber is movably mounted to said frame, said comber is adapted to create slack in said cord;
   f) said punch pin is movably mounted to said frame, said punch pin is adapted to receive said cord and penetrate said material;
   g) said punch pin pulls said cord from said first side of said material through to said second side of said material;
   h) said punch pin is adapted to form an open loop on said second side of said material; and
   i) said spear draws said cord through said open loop.

* * * * *

UNITED STATES PATENT AND TRADEMARK OFFICE
CERTIFICATE OF CORRECTION

| | | |
|---|---|---|
| PATENT NO. | : 7,011,033 B2 | Page 1 of 1 |
| APPLICATION NO. | : 10/610075 | |
| DATED | : March 14, 2006 | |
| INVENTOR(S) | : Sargent, Jr. et al. | |

It is certified that error appears in the above-identified patent and that said Letters Patent is hereby corrected as shown below:

Column 10, line 10, "damper" should read --clamper--.

Column 10, line 14, "damper" should read --clamper--.

Signed and Sealed this

Seventeenth Day of April, 2007

JON W. DUDAS
*Director of the United States Patent and Trademark Office*